(12) United States Patent
Mori et al.

(10) Patent No.: US 9,217,139 B2
(45) Date of Patent: Dec. 22, 2015

(54) EXTRACELLULARLY SECRETED NUCLEASE

(75) Inventors: Kozue Mori, Yokosuka (JP); Yukari Ohta, Yokosuka (JP); Yuji Hatada, Yokosuka (JP); Nobuyuki Nakamura, Yokosuka (JP); Masayuki Miyazaki, Yokosuka (JP)

(73) Assignee: JAPAN AGENCY FOR MARINE-EARTH SCIENCE AND TECHNOLOGY, Yokosuka-shi (JP)

( * ) Notice: Subject to any disclaimer, the term of this patent is extended or adjusted under 35 U.S.C. 154(b) by 0 days.

(21) Appl. No.: 13/823,990

(22) PCT Filed: Sep. 15, 2011

(86) PCT No.: PCT/JP2011/071132
§ 371 (c)(1),
(2), (4) Date: Mar. 15, 2013

(87) PCT Pub. No.: WO2012/036241
PCT Pub. Date: Mar. 22, 2012

(65) Prior Publication Data
US 2013/0189760 A1    Jul. 25, 2013

(30) Foreign Application Priority Data
Sep. 16, 2010   (JP) .................. 2010-207598

(51) Int. Cl.
| | |
|---|---|
| *C12N 9/22* | (2006.01) |
| *C12R 1/465* | (2006.01) |
| *C12Q 1/44* | (2006.01) |
| *C12N 1/08* | (2006.01) |

(52) U.S. Cl.
CPC .. *C12N 9/22* (2013.01); *C12N 1/08* (2013.01); *C12Q 1/44* (2013.01); *C12R 1/465* (2013.01)

(58) Field of Classification Search
CPC .............................. C12N 9/22; C12N 2830/55
USPC ...................................... 435/199, 253.5, 270
See application file for complete search history.

(56) References Cited

PUBLICATIONS

Nicieza et al., Purification, Characterization, and Role of Nucleases and Serine Proteases in Streptomyces Differentiation. The Jnl. Bio. Chem. 274: 29, 20366-20375, 1999.*
Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Whisstock et al., Prediction of protein function from protein sequence and structure. Quart. Rev. BioPhys. 36: 307-340, 2003.*

* cited by examiner

*Primary Examiner* — Tekchand Saidha
(74) *Attorney, Agent, or Firm* — Birch, Stewart, Kolasch & Birch, LLP

(57) ABSTRACT

The purpose of the present invention is to provide a nuclease that secretes natural nonpathogenic microorganisms extracellularly, has higher specific activity than conventional nucleases, and is useful in nucleolytic degradation on an industrial scale. This purpose is achieved with an extracellularly secreted nuclease derived from *Streptomyces* bacteria, the nuclease having specific activity equal to or greater than the specific activity of Benzonase® when supplied to double-stranded DNA for 30 minutes at 37° C. in 20 mM Tris/HCl (pH 8.5) containing 1 mM $MgCl_2$ and 1 mM $CaCl_2$ after purification, using double-stranded DNA, single-stranded DNA, and RNA as substrates.

8 Claims, 17 Drawing Sheets

EXTRACELLULARLY SECRETED NUCLEASE

CROSS-REFERENCE TO RELATED APPLICATIONS

The present application claims priority from Japanese Patent Application No. 2010-207598 filed on Sep. 16, 2010. The entire contents of this application are incorporated herein by reference.

TECHNICAL FIELD

The present invention relates to novel extracellular secretion-type nucleases and methods of producing the novel extracellular secretion-type nucleases, as well as to novel bacteria of the genus *Streptomyces* that are used by the production method. Moreover, the present invention relates to methods of degrading nucleic acids with the use of the extracellular secretion-type nucleases.

BACKGROUND ART

The term "Nuclease" means an all-inclusive term of nucleolytic enzymes that specifically degrades nucleic acids. When a nuclease reacts with nucleic acids such as deoxyribonucleic acid and ribonucleic acid, a phosphodiester bond between sugar and phosphate in the nucleic acids is hydrolyzed, and nucleosides are generated.

Nucleases are categorized as one type of ester hydrolase whose EC number (Enzyme Commission number) is EC. 3.1. Moreover, the nucleases are categorized into ribonucleases, which decompose RNA, and deoxyribonucleases, which decompose DNA. Furthermore, the nucleases may be categorized according to the type of decomposition.

An enzyme that serves as a catalyst to cleavage nucleic acids from the inside (endo-) of a sequence of the nucleic acids is called endonuclease. Various restriction enzymes are among typical endonucleases. While, an enzyme that serves as a catalyst to cleavage nucleic acids in such a way as to shave from a 5' or 3' end of the nucleic acids from the outside (exo-) to the inside of a sequence of the nucleic acids is called exonuclease. Exonuclease III and the like are known as typical exonucleases.

Nucleases are now used in various scenes from laboratory scale to industrial scale. For example, the use of nucleases makes it possible to decrease the viscosity of cell extracts because of nucleic-acid degradation activity thereof. Accordingly, if nucleases are used when proteins and other objective substances in the cell extracts are isolated and purified, the following advantages can be expected: shortening of process time, an improvement in the amount of objective substances obtained, an improvement in fractionation by centrifugal separation method (isolation of pellet and supernatant), smooth filtration of a solution (particularly ultrafiltration), an improvement in the efficiency of chromatographic process and the like. Moreover, if nucleases are used when viruses, inclusion bodies, or the like to which nucleic acids are nonspecifically adsorbed are isolated and purified, an improvement can be expected to be made in the yield of the above entities. Furthermore, if nucleases are used in a process of preparing samples used in assays such as ELISA, chromatography, 2D-PAGE, and footprint analysis for the analysis of biological samples, it is possible to avoid measurement error associated with unnecessary nucleic acids.

As a nuclease that can be used in such various scales or scenes, an endonuclease derived from *Serratia* spp (*Serratia* spp.) is known (See the specification of Japanese Patent No. 2604365 and the specification of U.S. Pat. No. 5,173,418 as Patent Documents 1 and 2, respectively; the contents of Patent Documents 1 and 2 are incorporated herein by reference). Microorganisms of the genus *Serratia* may contain disease-causing bacteria as opportunistic infection bacteria. Therefore, the endonuclease disclosed in Patent Document 1 is produced as an extracellular secretion-type enzyme, which is secreted outside a cell, with the use of *Escherichia coli* by gene-recombination technology. Incidentally, the endonuclease derived from *Serratia* spp disclosed in Patent Document 1 is marketed under the brand of Benzonase (Registered Trademark) (See, as Non-Patent Document 1, "Benzonase—a unique endonuclease—," [online], Jan. 1, 2008, Merck Ltd., [Searched on Jul. 30, 2010], Internet <URL: http://www2.merck.co.jp/japan/chemical/pdf/info_pdf/071225_Ben zonase_16p.pdf>"; the contents of Non-Patent Document 1 are incorporated herein by reference).

Example of nucleases derived from non-pathogenic microorganisms, a nuclease produced by bacteria of the genus *Streptomyces* (*Streptomyces* spp.), which is one type of actinomycetes, is known (See the following documents as Non-Patent Documents 2 to 7: Biochem. J. 1995 306, 93-100; Biochem. J. 1992 281, 231-237; Appl Microbiol Biotechnol. 1995 November; 43(6): 1056-1060; Biochimica et Biophysica Acta (BBA)—General Subjects, Volume 1721, Issues 1-3, 18 Jan. 2005, 116-123; FEMS Microbiology Letters, Volume 237, Issue 2, 15 Aug. 2004, 273-278; and Process Biochemistry Volume 40, Issues 3-4, March 2005, 1271-1278; the contents of Non-Patent Documents 2 to 7 are incorporated herein by reference). The nucleases disclosed in Non-Patent Documents 2 and 3 are produced as intracellular accumulation-type enzymes. Whereas, the nucleases disclosed in Non-Patent Documents 4 to 7 are extracellular secretion-type enzymes which are secreted out of cells.

PRIOR ART DOCUMENTS

Patent Documents

Patent Document 1: Japanese Patent No. 2604365
Patent Document 2: U.S. Pat. No. 5,173,418

Non-Patent Documents

Non-Patent Document 1: "Benzonase—a unique endonuclease—," [online], Jan. 1, 2008, Merck Ltd., [Searched on Jul. 30, 2010], Internet <URL: http://www2.merck.co.jp/japan/chemical/pdf/info_pdf/071225_Benzonase_16p.pdf>
Non-patent Document 2: Santiago CAL, Jesus F. APARICIO, Clara G. DE LOS REYES-GAVILAN, Rebeca G. NICIEZA and Jesus SANCHEZ, Biochem. J. 1995 306, 93-100
Non-Patent Document 3: Jesus F. APARICIO, Carlos HARDISSON and Jesus SANCHEZ, Biochem. J. 1992 281, 231-237
Non-Patent Document 4: Vukelic B, Ritonja A, Vitale L., Appl Microbiol Biotechnol. 1995 November; 43(6):1056-1060
Non-Patent Document 5: Zuzana Brnakova, Andrej Godany and Jozef Timko, Biochimica et Biophysica Acta (BBA)—General Subjects, Volume 1721, Issues 1-3, 18 Jan. 2005, 116-123
Non-Patent Document 6: Sumedha S. Deshmukh and Vepatu Shankar, FEMS Microbiology Letters, Volume 237, Issue 2, 15 Aug. 2004, Pages 273-278

Non-Patent Document 7: Nitin S. Patil, Sumedha S. Deshmukh and Vepatu Shankar, Process Biochemistry Volume 40, Issues 3-4, March 2005, Pages 1271-1278

DISCLOSURE OF THE INVENTION

Problems to be Solved by the Invention

The nucleases disclosed in Patent Documents 1 and 2, and Benzonase disclosed in Non-Patent Document 1 are produced by using non-pathogenic microorganisms. However, the above nucleases are produced from genetically-engineered *Escherichia coli*. Therefore, the productivity of the nucleases is lower than the productivity of the nucleases derived from the native bacteria. Accordingly, in order to obtain the nucleases on an industrial scale, a production process needs to be repeated, or carried out for a long period of time. There are problems in that burdens increase in terms of work, economics, and time. Therefore, it is desirable as for a method of producing the nucleases that gene-recombination technology be not used, and that the nucleases be produced by using natural non-pathogenic microorganisms.

The nucleases disclosed in Non-Patent Documents 2 and 3 are enzymes of an intracellular accumulation type that are accumulated in non-pathogenic microorganisms. Thus, in order to obtain the above nucleases, there is a need for crushing the microorganisms in which the nucleases are accumulated followed by separating and purifying the nucleases from the obtained debris of microorganisms. Accordingly, there are problems in that the steps of obtaining the nucleases disclosed in Non-Patent Documents 2 and 3 are complicated, and the probability is high that impurities get mixed in.

Whereas, the nucleases disclosed in Non-Patent Documents 4 to 7 are enzymes of an extracellular secretion-type that are secreted out of non-pathogenic microorganisms. The problems appeared in the course of producing the nucleases disclosed in Patent Documents 1 and 2 as well as Non-Patent Documents 1 to 3 as described above do not arise.

However, the nucleases disclosed in Non-Patent Documents 4 to 7 have a common problem: extremely low levels of activity. The specific activities of the nucleases disclosed in Non-Patent Documents 4 to 7 are $3.5 \times 10^5$ U/mg-protein, $9.7 \times 10^3$ U/mg-protein, $1.3 \times 10^4$ U/mg-protein, and $3.2 \times 10^4$ U/mg-protein, respectively, in the unit described in Non-Patent Document 1. In this manner, the specific activities of the nucleases disclosed in Non-Patent Documents 4 to 7 are about 3 to 100 times lower than the nuclease disclosed in Non-Patent Document 1.

The nucleases disclosed in Non-Patent Documents 4 and 5 are prone to enzyme activity inhibition by NaCl. In the presence of 10 mM of NaCl, the specific activity of the nuclease disclosed in Non-Patent Document 4 is 32 percent compared with a standard activity condition described in Non-Patent Document 4. In the presence of 100 mM of NaCl, the specific activity of the nuclease disclosed in Non-Patent Document 5 is 40 percent to 50 percent compared with a standard activity condition described in Non-Patent Document 5. Accordingly, in the course of diluting the nucleases disclosed in Non-Patent Documents 4 and 5, a typical, widely-used NaCl-containing buffer solution such as PBS cannot be employed. In an industrial production process that goes through culture of microorganisms, microorganisms are usually cultured with the use of a high-nutrient medium that contains 100 mM or more of monovalent metal salt to increase the bacteria turbidity. The degradation of nucleic acids in a broth obtained from such culture may be carried out under the condition that the concentration of salt is high.

If the nucleases disclosed in Non-Patent Documents 6 and 7 are dialyzed by EDTA as purified enzyme, the activity of the nucleases is completely lost. In order to restore the activity, $Mn^{2+}$ is required; other divalent metal ions such as $Mg^{2+}$ cannot substitute for $Mn^{2+}$. Manganese salt is quite expensive, and poses a risk of residual toxicity.

In that manner, there are problems in that the nucleases disclosed in Non-Patent Documents 4 to 7 are low in specific activity, prone to enzyme activity inhibition by NaCl, and limited to $Mn^{2+}$ for a divalent metal ion required for enzyme activity. Due to the above problems, the nucleases have not been used in degradation of nucleic acids on an industrial scale.

Accordingly, a first problem to be solved by the present invention is to provide a nuclease by which natural non-pathogenic microorganisms are secreted out of cells, and which is higher in specific activity than a conventional nuclease and effective in degradation of nucleic acids on an industrial scale. A second problem to be solved by the present invention is to provide a nuclease by which natural non-pathogenic microorganisms are secreted out of cells, and which has a smaller effect of NaCl on enzyme activity and requires a divalent metal ion that is less expensive and toxic than manganese as for enzyme activity, and which is effective in degradation of nucleic acids on an industrial scale. Still another problem to be solved by the present invention is to provide a method of producing the above nuclease, and a non-pathogenic microorganism that can be used for the method.

Means of Solving the Problems

As a result of extensive studies, the present inventors succeeded in isolating, from the deep sea, a microorganism that secretes a high specific-activity nuclease into a broth. Results obtained by identifying the microorganism showed that the microorganism is non-pathogenic bacteria of the genus *Streptomyces*, which is one type of actinomycetes. The microorganism was named *Streptomyces* sp. MBE174 by the present inventors.

From a broth of *Streptomyces* sp. MBE174, a protein fraction showing nuclease activity was separated and purified. As a result, the following two types nucleases were obtained: a nuclease (NucS) which works on double-stranded DNA, single-stranded DNA, and RNA as substrate, and is higher in specific activity than Benzonase disclosed in Non-Patent Document 1; and a nuclease (NucL) which can works on double-stranded DNA and single-stranded DNA as substrate, keeps a specific activity thereof in the presence of high-concentration $Na^+$, and requires magnesium that is less expensive and toxic than manganese.

The above NucS and NucL were secreted into a broth with the nuclease activity thereof maintained as *Streptomyces* sp. MBE174 proliferated. Accordingly, the broth of *Streptomyces* sp. MBE174, as well as substances obtained by drying the broth and those obtained by simple purification, is highly effective and can be used in degradation of nucleic acids on an industrial scale as crude enzymes containing two types of nuclease, NucS and NucL.

The present invention is an invention completed based on the above findings.

According to the present invention, what is provided as a nuclease of a first aspect of the present invention is an extracellular secretion-type nuclease derived from bacteria of the genus *Streptomyces*, wherein substrates of the nuclease includes double-stranded DNA, single-stranded DNA, and RNA, and the nuclease has a specific activity that is almost equal to or higher than the specific activity of Benzonase (Registered Trademark) when the nuclease is purified and then supplied to double-stranded DNA for 30 minutes at 37 degrees Celsius in 20 mM of Tris/HCl at pH 8.5 that contains 1 mM of $MgCl_2$ and 1 mM of $CaCl_2$.

Preferably, a molecular weight of the nuclease is 17,000 to 21,000 according to SDS-PAGE method.

Preferably, the nuclease requires $Mg^{2+}$ or $Mn^{2+}$ as divalent metal ion.

Preferably, the bacteria of the genus *Streptomyces* are *Streptomyces* sp. MBE174 (Receipt Number: FERM P-21987).

According to another aspect of the present invention, what is provided as a nuclease of a second aspect of the present invention is a nuclease containing, (1) an amino acid sequence disclosed in SEQ ID NO. 1 of a sequence list, (2) an amino acid sequence containing one or a plurality of amino acids lacked, replaced or added in the amino acid sequence disclosed in SEQ ID NO. 1 of the sequence list, or (3) an amino acid sequence having 90 percent or more homology to the amino acid sequence disclosed in SEQ ID NO. 1 of the sequence list.

According to another aspect of the present invention, what is provided as a nuclease of a third aspect of the present invention is an extracellular secretion-type nuclease derived from bacteria of the genus *Streptomyces*, wherein substrates of the nuclease includes double-stranded DNA and single-stranded DNA, and a specific activity of the nuclease in the presence of 100 mM of $Na^+$ is equal to or more than 60 percent compared with the specific activity of the nuclease in the case where $Na^+$ is not added.

Preferably, a molecular weight of the nuclease is about 66,500 according to SDS-PAGE method.

Preferably, the nuclease requires $Mg^{2+}$ as divalent metal ion.

Preferably, the bacteria of the genus *Streptomyces* are *Streptomyces* sp. MBE174 (Receipt Number: FERM P-21987).

According to another aspect of the present invention, what is provided as a nuclease of a fourth aspect of the present invention is a nuclease containing, (a) an amino acid sequence disclosed in SEQ ID NO. 2 of the sequence list, (b) an amino acid sequence containing one or a plurality of amino acids lacked, replaced or added in the amino acid sequence disclosed in SEQ ID NO. 2 of the sequence list, or (c) an amino acid sequence having 85 percent or more homology to the amino acid sequence disclosed in SEQ ID NO. 2 of the sequence list.

According to another aspect of the present invention, what is provided is a crude enzyme containing, as nuclease active substance, the nuclease of the first or second aspect of the present invention and/or the nuclease of the third or fourth aspect of the present invention.

According to another aspect of the present invention, what is provided is a method of producing an extracellular secretion-type nuclease containing a step of culturing *Streptomyces* sp. MBE174 (Receipt Number: FERM P-21987) to obtain at least one type of extracellular secretion-type nuclease.

According to another aspect of the present invention, what is provided is an extracellular secretion-type nuclease or crude enzyme thereof obtained by the production method of the present invention.

According to another aspect of the present invention, what is provided is *Streptomyces* sp. MBE174 (Receipt Number: FERM P-21987).

According to another aspect of the present invention, what is provided is a method of degrading nucleic acids containing a step of degrading nucleic acids by subjecting the nuclease of the first or second aspect of the present invention and/or the nuclease of the third or fourth aspect of the present invention to a sample containing nucleic acids.

Preferably, the nucleic acids are DNA.

Effects of the Invention

A nuclease of the present invention is secreted out of a cell by one type of bacteria of the genus *Streptomyces* that is a natural non-pathogenic microorganism. Therefore, a broth of bacteria of the genus *Streptomyces* that produce the nuclease of the present invention, as well as substances obtained by drying the broth and those obtained by crude purification of the broth, can be used as crude enzymes. The nuclease of the present invention is also higher in specific activity than conventional nucleases. Moreover, the nuclease of the present invention has a feature that can maintain activity even in the presence of high salt concentration, with magnesium as a required divalent metal ion. Thus, the nuclease of the present invention can be used in degradation of nucleic acids on an industrial scale.

Two types of nuclease of the present invention can be independently used, for example, according to salt concentration. More specifically, in a low-salt-concentration environment, the use of one enzyme (e.g. NucS) having a higher level of specific activity makes it possible to promptly degrade DNA and RNA. In a high-salt-concentration environment, the use of the other enzyme (e.g. NucL) is expected to enable degradation of DNA and accumulation of RNA. Accordingly, if a mixture of the two types of nuclease of the present invention is prepared, it is possible to achieve degradation and accumulation of desired nucleic acids by changing the salt concentration.

Furthermore, an enzyme (e.g. NucL) of the present invention that maintains activity in a high-salt-concentration environment can degrade DNA without degrading RNA. By making use of the characteristic of the enzyme that does not degrade RNA, for example, it is possible to apply the enzyme of the present invention to a method of specifically preparing RNA.

If the nuclease of the present invention is used in isolation and purification of protein and other objective substances in cell extract, the following advantages can be expected: shortening of process time, an improvement in the amount of objective substances obtained, an improvement in fractionation by centrifugal separation method (isolation of pellet and supernatant), smooth filtration of a solution (in particular ultrafiltration), an improvement in the efficiency of chromatographic process, an improvement in the yield of viruses, inclusion bodies, or the like, and avoidance of measurement error in methods such as ELISA, chromatography, 2D-PAGE, and footprint analysis.

MODE FOR CARRYING OUT THE INVENTION

Figure 1:
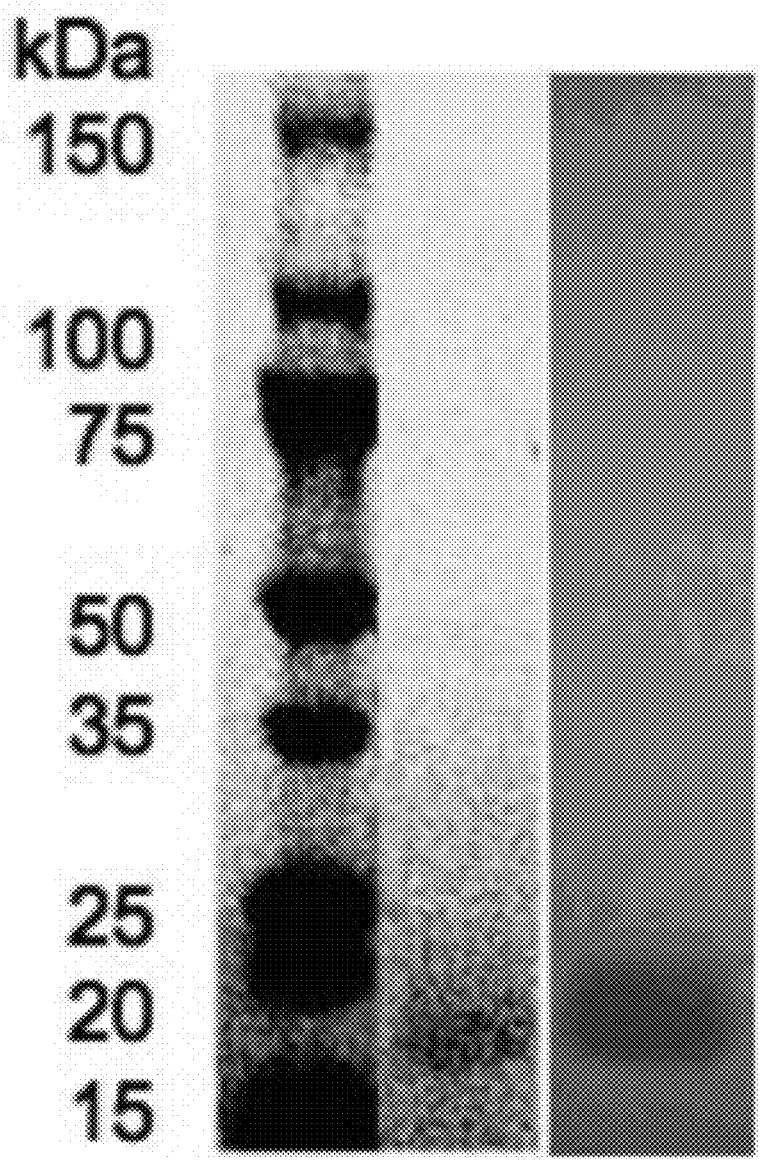
FIG. 1 is a diagram showing SDS-PAGE and activity staining of partially purified NucS.

Hereinafter, the present invention will be described in detail.

Nucleases of the present invention relate to an extracellular secretion-type nuclease derived from bacteria of the genus *Streptomyces*. The nucleases of the present invention are categorized into two enzyme groups according to the feature, function, and structure. In the following description, the nucleases of the present invention are referred to as "nuclease A" and "nuclease B."

[1] Nuclease A of the Present Invention

Nuclease A of the present invention relates to a nuclease that works on double-stranded DNA, which includes for example double-stranded DNA of a supercoiled type, relaxed type, and the like, single-stranded DNA, and RNA as substrate. The nuclease A of the present invention is characterized in that a specific activity of the nuclease A is almost equal to or higher than the specific activity of Benzonase (Registered Trademark) after the nuclease A is supplied to double-stranded DNA for 30 minutes at 37 degrees Celsius after purification in 20 mM of Tris/HCl at pH 8.5 that contains 1 mM of $MgCl_2$ and 1 mM of $CaCl_2$.

In the present specification, "Benzonase (Registered Trademark)" means a commercially available nuclease that is described in Non-Patent Document 1 as product name "Benzonase Grade I (99%) 250 U/μL for biotechnology." The specific activity of Benzonase (Registered Trademark) is 9.4× $10^5$ U/mg-protein at a time when Benzonase is subjected to double-stranded DNA for 30 minutes at 37 degrees Celsius in 20 mM of Tris/HCl at pH 8.5 that contains 1 mM of $MgCl_2$ and 1 mM of $CaCl_2$ as shown in Examples as described later.

In the present specification, as for the phrase "almost equal to the specific activity of Benzonase (Registered Trademark)," the specific activity is not specifically restricted as long as the value of the specific activity approximates to the specific activity of Benzonase. The specific activity is, for example, within ±10 percent of the specific activity of Benzonase, preferably ±5 percent, or more preferably ±2 percent.

In the present specification, as for the phrase "higher than the specific activity of Benzonase (Registered Trademark)," the specific activity is not specifically restricted as long as the specific activity is higher than the specific activity of Benzonase. The specific activity is, for example, 1.1 times larger than the specific activity of Benzonase, preferably 1.5 times larger, more preferably 2.0 times larger, even more preferably 2.5 times larger, or still more preferably 3.0 times larger.

When a comparison is made with the specific activity of Benzonase, the purified nuclease A of the present invention is used. Purification of the nuclease A of the present invention is carried out by using anion exchange (SuperQ), hydroxyapatite, cation exchange (CM Sepharose), heparin affinity, and gel filtration chromatography. According to a preferred aspect of the present invention, NucS, which is described in Examples as described later, has a specific activity of 3.6× $10^6$ U/mg-protein after purification. While, the specific activity of Benzonase (Registered Trademark) is 9.4× $10^5$ U/mg-protein. Accordingly, it is preferred that after purification, the specific activity of the nuclease A of the present invention be about 3.8 times larger than the specific activity of Benzonase.

The substrate specificity of the nuclease A of the present invention is measured by using various nucleic acids such as double-stranded DNA, single-stranded DNA, and RNA as substrates, and subjecting to the substrates for 30 minutes at 37 degrees Celsius in 20 mM of Tris/HCl at pH 8.5 that contains 1 mM of $MgCl_2$ and 1 mM of $CaCl_2$ followed by looking into the degradation activity of the substrates.

The nuclease A of the present invention is not specifically restricted as long as the substrates and specific activity are those as described above. Preferably, a molecular weight of the nuclease A is 17,000 to 21,000 according to SDS-PAGE method, and/or the nuclease requires $Mg^{2+}$ or $Mn^{2+}$ as divalent metal ion.

The nuclease A of the present invention can be isolated by screening methods that include the steps of using, as indicators, not only the catalytic activity for the substrates and the specific activity but also the molecular weight, the divalent metal requirement and the like that are described above and examining nuclease activity in culture supernatant obtained by culturing bacteria of the genus *Streptomyces* which are for example bacteria of the genus *Streptomyces* that inhabit the deep sea (200 m or more below the surface of the ocean). Preferably, the bacteria of the genus *Streptomyces* that inhabit the deep sea are *Streptomyces* sp. MBE174. Incidentally, *Streptomyces* sp. MBE174 was deposited in the International Patent Organism Depositary of the National Institute of Advanced Industrial Science and Technology (Tsukuba Central 6, 1-1, Higashi 1-chome, Tsukuba-shi, Ibaraki-ken, 305-8566, Japan) with Receipt Number FERM P-21987 on Jul. 27, 2010.

A specific aspect of the nuclease A of the present invention is a nuclease containing: (1) an amino acid sequence disclosed in SEQ ID NO. 1 of a sequence list; (2) an amino acid sequence obtained by lacking or replacing one or a plurality of amino acids of the amino acid sequence disclosed in SEQ ID NO. 1 of the sequence list, or adding one or a plurality of amino acids to the amino acid sequence disclosed in SEQ ID NO. 1 of the sequence list; or (3) an amino acid sequence having 90 percent or more homology to the amino acid sequence disclosed in SEQ ID NO. 1 of the sequence list.

The nuclease that contains the amino acid sequence (1) disclosed in SEQ ID NO. 1 of the sequence list is a group of enzymes with a molecular weight of 17,000 to 21,000 according to SDS-PAGE method; and includes, as common sequence, ALPTPVSAATAR (SEQ ID NO. 27 of the sequence list). SEQ ID NO. 1 of the sequence list represents a common amino acid sequence (157 amino acids) that is calculated as 17 kDa, with common amino acid sequence ALPTPVSAATAR as origin of N-terminal. A more specific aspect of the nuclease A of the present invention is a nuclease that is NucS described in Examples as described later, and includes 214 amino acids (SEQ ID NO. 3 of the sequence list).

As for the phrase "one or a plurality of amino acids lacked, replaced or added" of the amino acid sequence (2), the range of "one or a plurality of" is not specifically restricted as long as the range allows the specific activity of a nuclease containing the amino acid sequence (2) after purification to be almost equal to or higher than the specific activity of Benzonase (Registered Trademark) under the condition that the nuclease A is subjected to double-stranded DNA for 30 minutes at 37 degrees Celsius in 20 mM of Tris/HCl at pH 8.5 that contains 1 mM of $MgCl_2$ and 1 mM of $CaCl_2$. The range, for example, means one to twenty, preferably one to ten, more preferably one to seven, even more preferably one to five, or particularly preferably about one to three. The phrase "an amino acid lacked" means lacking or disappearance of an amino acid residue in the sequence. The phrase "an amino acid replaced" means that an amino acid residue is replaced with another amino acid residue in the sequence. The phrase "an amino acid added" means that a new amino acid residue is added to the sequence.

A specific aspect of the phrase "one to a plurality of amino acids lacked, replaced and added" includes the situation where one to a plurality of amino acids are replaced with chemically similar other amino acids. For example, the following cases can be included: the case where a hydrophobic amino acid is replaced with another hydrophobic amino acid; and the case where a polar amino acid is replaced with another polar amino acid having the same electric charge. Such chemically similar amino acids are known in the art for each amino acid. Specific examples of non-polar (hydrophobic) amino acids include alanine, valine, isoleucine, leucine, proline, tryptophan, phenylalanine, and methionine. Specific examples of polar (neutral) amino acids include glycine, serine, threonine, tyrosine, glutamine, asparagines, and cysteine. Specific examples of (basic) amino acids having positive electric charge include arginine, histidine, and lysine. Specific examples of (acidic) amino acids having negative electric charge include asparagine acid and glutamic acid.

The term "homology" of the amino acid sequence (3) is in the range of 90 percent or more, preferably 93 percent or more, more preferably 95 percent or more, even more preferably 97 percent or more, or still more preferably 99 percent or more in such a way that the specific activity of a nuclease containing the amino acid sequence (3) after purification is almost equal to or higher than the specific activity of Benzonase (Registered Trademark) under the condition that the nuclease is subjected to double-stranded DNA for 30 minutes at 37 degrees Celsius in 20 mM of Tris/HCl at pH 8.5 that contains 1 mM of $MgCl_2$ and 1 mM of $CaCl_2$.

A method of obtaining the nuclease A of the present invention is not restricted. Besides the above-described screening methods, for example, the nuclease A may be synthesized physicochemically in reference to the disclosures of SEQ ID NO. 1 and No. 3 of the sequence list; or the nuclease A may be prepared in a genetic engineering manner from nucleic acids that code the amino acid sequences disclosed in SEQ ID NO. 1 and No. 3 of the sequence list.

[2] Nuclease B of the Present Invention

Nuclease B of the present invention relates to a nuclease that works on double-stranded DNA, which is for example double-stranded DNA of a supercoiled type, relaxed type, or the like, and single-stranded DNA as substrate, as well as does not substantially work on RNA as substrate.

The nuclease B of the present invention is characterized by having a specific activity that is, in the presence of 100 mM of $Na^+$, 60 percent or more, preferably 70 percent or more, even more preferably 80 percent or more, or still more preferably 90 percent or more of the specific activity of the case where $Na^+$ is not added.

The effects of $Na^+$ on the specific activity of the nuclease B of the present invention can be examined by measuring the nucleic-acid degradation activity at each level of NaCl concentration at 25 degrees Celsius in 10 mM of Tris/HCl at pH 8.5 that contains 1 mM of $MgCl_2$ and 0 to 100 mM of NaCl with the use of the following substrate: Deoxyribonucleic acid sodium salt from salmon testes 0.4 mg/mL (manufactured by Sigma-Aldrich; Cat no. D1626-1G).

The substrate specificity of the nuclease B of the present invention can be examined in the similar way as the substrate specificity of the nuclease A of the present invention.

The nuclease B of the present invention is not specifically restricted as long as the substrates and the stability thereof for $Na^+$ are those as described above. Preferably, a molecular weight thereof is about 66,500 according to SDS-PAGE method, and/or the nuclease requires $Mg^{2+}$ as divalent metal ion.

The nuclease B of the present invention uses can be isolated by screening methods that include the steps of using, as indicators, not only the catalytic activity for the substrates and the stability for $Na^+$ but also the molecular weight, the divalent metal requirement and the like, and examining nuclease activity in culture supernatant obtained by culturing bacteria of the genus *Streptomyces* which are for example bacteria of the genus *Streptomyces* that inhabit the deep sea (200 m or more below the surface of the ocean). Preferably, the bacteria of the genus *Streptomyces* that inhabit the deep sea are *Streptomyces* sp. MBE174 (Receipt Number: FERM P-21987).

A specific aspect of the nuclease B of the present invention is a nuclease containing: (a) an amino acid sequence disclosed in SEQ ID NO. 2 of the sequence list; (b) an amino acid sequence comprising one or a plurality of amino acids lacked, replaced or added in the amino acid sequence disclosed in SEQ ID NO. 2 of the sequence list; or (c) an amino acid sequence having 85 percent or more homology to the amino acid sequence disclosed in SEQ ID NO. 2 of the sequence list.

The nuclease that contains the amino acid sequence (a) disclosed in SEQ ID NO. 2 of the sequence list has a molecular weight of 66,500 according to SDS-PAGE method; and is a mature protein (575 amino acids) that does not contain signal peptide in an N-terminal portion. A more specific aspect of the nuclease B of the present invention is NucL described in Examples as described later, includes 607 amino acids (SEQ ID NO. 4 of the sequence list), and contains signal peptide in the N-terminal.

As for the phrase "one or a plurality of amino acids lacked, replaced or added" of the amino acid sequence (b), the range of "one or a plurality of" is not specifically restricted as long as the range allows the specific activity of a nuclease containing the amino acid sequence (b) in the presence of 100 mM of $Na^+$ to be 60 percent or more of the specific activity of the case where $Na^+$ is not added. The range, for example, means one to twenty, preferably one to ten, more preferably one to seven, even more preferably one to five, or particularly preferably about one to three. The meanings of the phrases "an amino acid lacked," "an amino acid replaced," and "an amino acid added" in the amino acid sequence (b), as well as of a specific embodiment of the phrase "one or a plurality of amino acids lacked, replaced or added," are the same as those described above with respect to the amino acid sequence (2) that is a specific aspect of the nuclease A of the present invention.

The term "homology" of the amino acid sequence (c) is in the range of 85 percent or more, preferably 88 percent or more, more preferably 90 percent or more, even more preferably 95 percent or more, or still more preferably 99 percent or more in such a way that the specific activity of a nuclease containing the amino acid sequence (c) in the presence of 100 mM of $Na^+$ is 60 percent or more of the specific activity in the case where $Na^+$ is not added.

A method of obtaining the nuclease B of the present invention is not restricted. Besides the above-described screening methods, for example, the nuclease B may be synthesized physicochemically in reference to the disclosures of SEQ ID NO. 2 and No. 4 of the sequence list; or the nuclease B may be prepared in a genetic engineering manner from nucleic acids that code the amino acid sequences disclosed in SEQ ID NO. 2 and No. 4 of the sequence list.

[3] Crude Enzyme of the Present Invention

A crude enzyme of the present invention contains, as nuclease active substance, the nuclease A of the present invention, or the nuclease B of the present invention, or the two types of nuclease. In the crude enzyme of the present invention, the abundance ratio of nuclease A to nuclease B of the present invention is not specifically restricted. The abundance ratio can be appropriately selected according to the types and concentration of nucleic acids that serve as substrate, the types and concentration of substances that affect the activity of the nucleases, and other factors.

The crude enzyme of the present invention shows the characteristics of the nuclease A of the present invention contained and/or the nuclease B of the present invention contained. According to the crude enzyme of the present invention, for example, in a low-salt-concentration environment, prompt degradation of DNA and RNA can be expected from the use of the nuclease A of the present invention having a high level of specific activity. In a high-salt-concentration environment, the use of the nuclease B of the present invention can be expected to enable degradation of DNA and accumulation of RNA. Therefore, the use of the crude enzyme of the present invention makes it possible to achieve degradation and accumulation of desired nucleic acids by changing the salt concentration.

The crude enzyme of the present invention can be produced as a culture that is obtained by culturing bacteria of the genus Streptomyces that produce the nuclease A and nuclease B of the present invention, or preferably Streptomyces sp. MBE174 (Receipt Number: FERM P-21987).

[4] Production Method of the Present Invention

A production method of the present invention is a method of producing an extracellular secretion-type nuclease, including a step of culturing Streptomyces sp. MBE174 (Receipt Number: FERM P-21987) to obtain at least one type of extracellular secretion-type nuclease. Specifically, the method of producing the extracellular secretion-type nuclease includes steps of inoculating Streptomyces sp. MBE174 (Receipt Number: FERM P-21987) onto an appropriate medium by usual technique; culturing the inoculated bacteria under an appropriate condition; and obtaining an extracellular secretion-type nuclease from a culture obtained. It is preferred that the extracellular secretion-type nuclease be the nuclease A of the present invention and/or nuclease B of the present invention.

The production method of the present invention is largely divided into two steps and thus contain: (a) a step of culturing Streptomyces sp. MBE174 (Receipt Number: FERM P-21987) to obtain a culture containing an extracellular secretion-type nuclease; and (b) a step of obtaining the extracellular secretion-type nuclease from the culture.

As for a nutrient medium that is used to culture Streptomyces sp. MBE174 (Receipt Number: FERM P-21987), those known as medium for bacteria of the genus Streptomyces can be widely used. For example, the following synthetic media are available: a YMA (Yeast extract-Malt extract Agar) medium (4.0 g/l of yeast extract, 10.0 g/l of malt extract, 4.0 g/l of glucose, and 18.0 g/l of agar; pH 7.3); an albumin medium (0.25 g/l of egg albumin, 1.0 g/l of glucose, 0.5 g/l of $K_2HPO_4$, 0.2 g/l of $MgSO_4 \cdot 7H_2O$, 1 ml of a one-percent $Fe_2(SO_4)_3$ solution, and 18.0 g/l of agar; pH 6.8 to 7.0); and the like. Moreover, a natural medium is also available. Preferably, the natural medium includes 4.0 g/l of yeast extract, 10.0 g/l of malt extract, 30.0 g/l of glucose, 50.0 g/l of polypeptone S, and 6.0 g/l of calcium carbonate, with no pH adjustments. In addition, in the case where the culture is used by itself as crude enzyme, when the medium is prepared, attention needs to be paid to pH and the concentrations of compounds such as monovalent salt, divalent metal salt, phosphate, and other substances which affect enzyme activities. It is preferred that the concentrations be increased or decreased according to desired nuclease activity.

As for a culture method, a liquid culture method (a shaking culture method, or an aerated and agitated culture method) is preferred; the aerated and agitated culture method is preferred for industrial use. The culturing of Streptomyces sp. MBE174 (Receipt Number: FERM P-21987) is aerobically carried out usually under a condition selected from: a temperature of 20 to 45 degrees Celsius, or preferably 25 to 40 degrees Celsius, and pH 5 to 9, or preferably 6 to 8. The culture time may be equal to or greater than the time needed for Streptomyces sp. MBE174 (Receipt Number: FERM P-21987) to start proliferating. The culture time is preferably eight to 120 hours, or more preferably equal to the time required for a desired nuclease activity to reach a maximum value. A method of confirming bacteria proliferation is not specifically restricted. For example, a culture extracted may be observed under a microscope, or observed in terms of absorbancy. Furthermore, the dissolved oxygen concentration of a broth is not specifically restricted. However, usually, the dissolved oxygen concentration is preferably 0.5 to 20 ppm. Accordingly, a ventilation volume may be controlled, and stirring may be performed, and oxygen may be added to ventilation. The culture method may be of batch culture, feeding culture, continuous culture, or perfusion culture.

From a culture obtained by the above culture method, an extracellular secretion-type nuclease is extracted. A method of extracting an extracellular secretion-type nuclease can be carried out according to a typical enzyme extraction means. For example, after cells are removed by a commonly known means such as solid-liquid separation, culture supernatant can be used as crude enzyme. For the solid-liquid separation, commonly known methods may be employed without restriction. For example, the following methods may be employed: a method of just carrying out centrifuge separation of the culture by itself; a method of carrying out filtration and separation by adding filter aid to the culture, or using a pre-coat filter in which filter aid is pre-coated or the like; and a method of carrying out membrane filtration and separation by using flat membrane, hollow fiber membrane, or the like.

The crude enzyme can be used without being changed. However, the crude enzyme may be purified before being used. For example, although not limited to those listed below, the crude enzymes can be subjected to each or a combination of the following commonly-known methods, to prepare purified enzymes for industrial use: a method of using a difference in heat resistance, such as thermal treatment; a method of using a difference in molecular weight, such as dialysis, ultrafiltration, resin column, gel filtration, gel filtration chromatography, and SDS-polyacrylamide gel electrophoresis; a method of using a difference in solubility, such as salt precipitation, ammonium sulfate precipitation, alcohol precipitation, and other kinds of solvent precipitation; a method of using a difference in electric charge, such as ion exchange chromatography that uses DEAE-TOYOPEARL resin or the like; a method of using specific affinity, such as affinity chromatography; a method of using a difference in hydrophobicity, such as reversed phase chromatography and hydrophobic chromatography that uses butyl-Toyopearl resin or the like; a method of using a difference in physical and chemical adsorption force, such as adsorption chromatography; and a method of using a difference in isoelectric point, such as isoelectric-point electrophoresis and isoelectric-point chromatography.

The crude enzyme and the purified enzyme can be immobilized. For example, the following methods may be employed: a method of binding to an ion exchanger; a method of covalently binding or adsorption to resin, membranes, and the like; and an inclusion method that uses high-molecular materials.

An extracellular secretion-type nuclease obtained by the production method of the present invention, or a crude enzyme thereof is provided as another aspect of the present invention. Moreover, *Streptomyces* sp. MBE174 (Receipt Number: FERM P-21987), that is bacteria of the genus *Streptomyces* used in the production method of the present invention, is also provided as another aspect of the present invention.

What is provided as another aspect of a production method of the present invention is a method of producing an extracellular secretion-type nuclease including: steps of synthesizing physicochemically, or in a genetic engineering manner, DNA fragments that code the nuclease A or B of the present invention by referencing a base sequence of DNA that codes the nuclease A of the present invention, which is for example a base sequence disclosed in SEQ ID NO. 5 of the sequence list, or a base sequence of DNA that codes the nuclease B of the present invention, which is for example a base sequence disclosed in SEQ ID NO. 6 of the sequence list; introducing the synthesized DNA fragments into a vector; inserting a recombinant vector, into which the DNA fragments are introduced, into a host cell to produce a transformant; and then culturing the transformant to obtain an extracellular secretion-type nuclease.

[5] Method of the Present Invention

A method of the present invention relates to a method of degrading nucleic acids, including a step of subjecting the nuclease A of the present invention or the nuclease B of the present invention, or both of them, to a sample containing nucleic acids to degrade the nucleic acids.

The nuclease A and nuclease B of the present invention can be used as solid or liquid crude enzyme and purified enzyme. The nuclease A and nuclease B of the present invention can also be used as immobilized enzyme, which is immobilized by commonly known method.

An aqueous medium in the sample containing the nucleic acids is not specifically restricted as long as the aqueous medium does not inhibit nucleic-acid degradation reaction. For example, the aqueous media include water and a buffer solution. As for the buffer solution, for example, the following may be employed: an acetate buffer solution, a phosphate buffer solution, a citrate buffer solution, a succinic buffer solution, a Tris-HCL buffer solution and the like. In addition, the activity of the nuclease A of the present invention can probably be inhibited by phosphate ion or sodium ion. Therefore, a Tris-HCL buffer solution that does not contain the above ion, or the like is preferred.

The amounts of the nuclease A and nuclease B of the present invention used are not specifically restricted. However, in terms of the efficiency of nucleic acid degradation and from an economic point of view, for example, the amount of the nuclease A of the present invention used is $1 \times 10^{-6}$ to 50 U (Unit) relative to 10 μg of nucleic acids, preferably $1 \times 10^{-5}$ to 10 U, more preferably $1 \times 10^{-4}$ to 1 U, or still more preferably $1 \times 10^{-3}$ to $1 \times 10^{-1}$ U; the amount of the nuclease B of the present invention used is $1 \times 10^{-4}$ to 50 U relative to 10 μg of nucleic acids, preferably $1 \times 10^{-3}$ to 20 U, more preferably $1 \times 10^{-2}$ to 10 U, or still more preferably $1 \times 10^{-1}$ to 1 U. The concentration of nucleic acids is not specifically limited as long as the nucleic acids can dissolve in the solution.

It is preferred that the nucleic-acid degradation reaction be carried out at a temperature around which the nuclease A and nuclease B of the present invention can have activity and be maintained in a stable manner, which is for example 25 to 35 degrees Celsius. Because it is preferred that pH of the nucleic-acid degradation reaction be achieved under a condition that enables the nuclease A and nuclease B of the present invention to have an activity and be maintained in a stable manner, which is, for example, suitable to be adjusted at 7.5 to 9.5. The reaction comes to an end at the time when sufficient degradation of nucleic acids is confirmed under the above condition. The reaction is usually completed for one to 100 hours.

If the sample containing nucleic acids contains a target substance after the nucleic-acid degradation reaction comes to an end, the target substance is isolated and purified, and the nuclease A and nuclease B of the present invention are separately recovered. Depending on the characteristics of the sample containing the target substance and nucleic acids, enzymes may be inactivated and the reaction may be stopped by appropriate means such as an operation of inactivating the enzymes by heating a reaction solution to 60 to 135 degrees Celsius, or preferably to 65 to 100 degrees Celsius, or an operation of decreasing pH (addition of acid such as hydrochloric acid).

It is assumed that the sample containing nucleic acids is a sample containing double-stranded DNA, single-stranded DNA, RNA, and the like. It is preferred that the sample be a sample containing DNA such as double-stranded DNA and single-stranded DNA which can be substrate of any one of the nuclease A and nuclease B of the present invention.

Hereinafter, the present invention will be described in more detail with reference to Examples. However, the present invention is not limited to Examples.

Examples

1. Detection by Activity Staining of Nucleolytic Enzyme that Exists in Culture Supernatant By screening with the nucleic-acid degradation activity for plasmid DNA as an indicator, *Streptomyces* sp. MBE174 (also referred to as MBE174, hereinafter), which was bacteria derived from the deep sea that produce and secrete a large amount of nucleolytic enzymes into culture supernatant, was isolated. It was found that the nucleolytic enzymes that the present strain produces in the culture supernatant are a plurality of proteins with a molecular weight of about 66.5 kDa and with a distribution in a low molecular weight region of 17 to 21 kDa as a result of SDS-PAGE and activity staining with the following as substrate: Deoxyribonucleic acid sodium salt from salmon testes (manufactured by Sigma-Aldrich; Cat no. D1626-1G).

2. Taxonomic Position of MBE174

The 16S rRNA gene sequence (1,483 base pairs) of MBE174 was analyzed. As a result, the gene sequence matched 99 percent of the following: *Streptomyces akiyoshiensis* NBRC12434$^T$ (AB184095), *S. viridochromogenes* NBRC3113$^T$ (AB184728), *S. paradoxus* NBRC14887$^T$ (AB184628), *S. collinus* NBRC12759$^T$ (AB184123), *S. griseoflavus* LMG19344$^T$ (AJ781322). Therefore, it was determined that the present strain was bacteria of the genus *Streptomyces*. Further taxonomic analysis is necessary to determine the species.

3. Purification of Low-Molecular-Weight Nucleolytic Enzyme Nuclease S

A low-molecular-weight nucleolytic enzyme (named Nuclease S; simply referred to as NucS, hereinafter) with a molecular weight of about 17 to 21 kDa was purified by using anion exchange (SuperQ), hydroxyapatite, cation exchange (CM Sepharose), heparin affinity (referring to FIG. 1), and gel filtration chromatography. The summary of purification is shown in Table 1.

TABLE 1

| | Total amount of protein (mg) | Total amount of activity (U) | Specific activity (U/mg) | Yield (%) |
|---|---|---|---|---|
| Culture supernatant | 2957.1 | 16202875 | 5479 | 100 |
| SuperQ | 133.1 | 4941820 | 41192 | 30.5 |
| Hydroxyapatite | 120.9 | 4667685 | 38596 | 28.8 |
| CM Sepharose | 1.2 | 2768077 | 2235929 | 17.1 |
| Heparin FF | 0.5 | 1502791 | 3237035 | 9.3 |
| Gel filtration KW802.5 | 0.3 | 1202233 | 3596705 | 7.4 |

The specific activity of NucS was measured at 37 degrees Celsius in 20 mM of Tris/HCl at pH 8.5 that contains 1 mM of MgCl$_2$ and 1 mM of CaCl$_2$ (a measurement method under the condition described here is also referred to as a standard specific activity measurement method, hereinafter); the specific activity was $3.6 \times 10^6$ U/mg-protein, which was a very high level of specific activity. In this case, 1 U represents an amount of enzymes necessary to increase the absorbancy of 260 nm by one for 30 minutes when the enzymes works on the following as substrate: Salmon sperm DNA 1 mg/mL (manufactured by Invitrogen; Cat no. 15632-011). As a reference, as for NucS, when the specific activity of Benzonase (Registered Trademark), which was a commercially available nucleolytic enzyme that had the highest specific activity among those listed in a brochure, was measured under the conditions described in the brochure (37 degrees Celsius) with the use of the same substrate; the specific activity was $9.4 \times 10^5$ U/mg-protein. As a result, it became clear that the specific activity of NucS is about 3.8 times higher than that of Benzonase.

The molecular weight was measured by gel filtration chromatography with the use of Superdex G75 (manufactured by GE Healthcare). An elution position corresponding to a molecular weight of about 16 kDa was confirmed as a peak top from a column. Since the value was much coincident with a molecular weight (about 17 to 21 kDa) of an enzyme produced on SDS-PAGE, it can be determined that NucS exists as monomer. The isoelectric point was measured by using Novex (Registered Trademark) IEF pH-3-10 gel (manufactured by Invitrogen); and pI was 10.

After SDS-PAGE, enzyme proteins were cut out according to molecular weight, and were subjected to LC-MS/MS analysis after tryptic digestion. In all the proteins cut out, peptide ALPTPVSAATAR (SEQ ID NO. 27 of the sequence list) containing a common amino acid sequence was detected. National Center for Biotechnology Information (NCBI, http://www.ncbi.nlm.nih.gov/), BLASTP programs 2.2.24+ (Cited Reference: Stephen F. Altschul, Thomas L. Madden, Alejandro A. Schaffer, Jinghui Zhang, Zheng Zhang, Webb Miller, and David J. Lipman (1997), Nucleic Acids Res. 25:33 89-3402; the contents of the document are incorporated herein by reference) was used to carry out homology search for Non-redundant protein database. As a result, the amino acid sequence matched a part of a secretion-type protein (secreted protein) with a molecular weight of 23 kDa (derived from *S. scabiei* 87.22, *S. griseoflavus* Tu4000, and others), which was registered in the database. Moreover, the amino acid sequence also showed homology (8/12 amino acids) to N-terminal sequence APPTPPDTATAR of a nucleolytic enzyme derived from *S. rimosus*, whose biochemical nature has already been made public. Based on the above results, it was determined that a group of low-molecular-weight nucleolytic enzymes with a molecular weight of 17 to 21 kDa produced by MBE174 was a product that was transcribed and translated from the same gene and then affected so as to become lower in molecular weight at C-terminal portion of the enzyme protein by protease or the like.

As a result of homology search by the above BLASTP programs 2.2.24+ with the use of the present amino acid sequence, the amino acid sequence completely matched an amino acid sequence partially contained not only in the above-mentioned secreted protein [derived from *Streptomyces griseoflavus* Tu4000] (Accession number ZP_05541504), but also in secreted protein, [derived from *Streptomyces avermitilis* MA-4680] (Accession number NP 827004), secreted protein [derived from *Streptomyces coelicolor* A3 (2)] (Accession number NP_626595.1), and the like. Then, base sequences that code the above amino acid sequences, and base sequences in the 1000 bp upstream and 1000 bp downstream regions thereof were acquired from the NCBI database; alignment was carried out by using software GENETYX (Registered Trademark)—MAC Version 12.1.0. Based on the present alignment base sequence, primer sets A (SEQ ID NO. 7 and No. 8 of the sequence list) and B (SEQ ID NO. 9 and No. 10 of the sequence list) including forward and reverse primers were designed. A forward primer and reverse primer of the primer set A were also referred to as primer set A F and primer set A R, respectively. The same rule was applied to primers used in any primer sets as described later. The entire DNA of MBE174 was used as a template to obtain about 0.3 kb of amplified DNA fragments through PCR with the use of the primer set A, as well as to obtain about 0.5 kb of amplified DNA fragments through PCR with the use of the primer set B. For the PCR reaction, TaKaRa LA Taq (Registered Trademark) polymerase (manufactured by TAKARA BIO) and a buffer that was supplied together with the product were used, and a method in which a cycle including thermal denaturation at 97 degrees Celsius for 20 seconds, annealing at 55 to 63 degrees Celsius for one minute, and elongation reaction at 72 degrees Celsius for 1.5 minutes was repeated 30 times, was used. Then, base sequences of the amplified fragments were analyzed. Based on the obtained base sequences, a primer set C (SEQ ID NO. 11 and No. 12 of the sequence list) was prepared. The entire DNA of MBE174 was used as a template to obtain about 0.3 kb of amplified DNA fragments through PCR with the use of the primer set C. The base sequences of the present fragment were analyzed. Based on the alignment base sequence and the base sequences obtained by base-sequence analysis of NucS, a primer set D (SEQ ID NO. 13 and No. 14 of the sequence list) was prepared. The entire DNA of MBE174 was used as a template to obtain about 0.3 kb of amplified DNA fragments through PCR with the use of the primer set D. Base sequences of the present fragments were analyzed, and a 5'-terminal sequence of nucS gene was obtained. Meanwhile, the entire DNA of MBE174 was digested by restriction enzyme PstI, and a PstI cassette, which was contained in TaKaRa LA PCR in vitro Cloning Kit (manufactured by TAKARA BIO; Cat no. RR015), was connected. The DNA mixture was used as a template to carry out PCR reaction with the use of the primer set E (SEQ ID NO. 15 and No. 16 of the sequence list). The obtained PCR reactant was used as a template, and the primer set F (SEQ ID NO. 17 and No. 18 of the sequence list) was also used to acquire about 1.2 kb of amplified fragments. A 3'-terminal base sequence of nucS gene was analyzed. All the base sequences of DNA amplified fragments that were obtained through PCR with the use of the above primer sets A to F were assembled to determine an entire-length base sequence (SEQ ID NO. 5 of the sequence list) of nucS gene. Among those closest to the gene sequence of the present enzyme, the gene sequence matched 88 percent (552/626 bases) of a region that codes putative secreted protein on a genome sequence of *S. coelicolor* A3 (2); 85 percent (533/623 bases) of a region that codes putative secreted protein on a genome sequence of *S. avermitilis* MA-4680; and 85 percent (533/624 bases) of a region that codes putative secreted protein on a genome sequence of *S. scabiei* 87.22. Among those closest to the amino acid sequence (SEQ ID NO. 3 of the sequence list) that the present gene codes, the amino acid sequence matched 83 percent (178/214 amino acids) of secreted protein of *S. coelicolor* A3(2); and 82 percent (177/214 amino acids) of secreted protein of *S. viridochromogenes* DSM40736 and *S. griseoflavus* Tu4000. As a result of searching directed to all the genes and proteins registered in the database, the base sequences that showed homology to the present gene and the amino acid sequence thereof were detected. However, there was no protein that was subjected to functional and enzymological analysis after isolation and purification, and had an example of report. Therefore, it is presumed that the NucS protein and the nucS gene have not been reported yet, and are new ones.

As described above, NucS, which had a molecular weight of about 17 to 21 kDa, had peptide ALPTPVSAATAR having a common amino acid sequence in all the proteins (as a result of cutting out all the proteins contained in a molecular region thereof after SDS-PAGE according to molecular weight, and subjecting the proteins to LC-MS/MS analysis after tryptic digestion). The molecular weight of NucS was about 17 kDa in the case where the molecular weight thereof was smallest according to SDS-PAGE method. Therefore, in the amino acid sequence (214 amino acids) of NucS, a common amino acid sequence (157 amino acids) that had common amino acid sequence ALPTPVSAATAR as origin of the N-terminal, and whose molecular weight was 17 kDa as a result of calculation was regarded as a core sequence (SEQ ID NO. 1 of the sequence list) of NucS. As a result of a comparison with the sequences registered in the database, the core sequence of NucS matched 86 percent (136/157 amino acids) of secreted protein of *Streptomyces griseoflavus* Tu4000 or S-layer domain-containing protein; and 85 percent (135/157 amino acids) of secreted protein of *Streptomyces coelicolor* A3(2), secreted protein of *Streptomyces lividans* TK24, and the like.

4. Purification of 66.5-kDa Nucleolytic Enzyme Nuclease L

Figure 2:
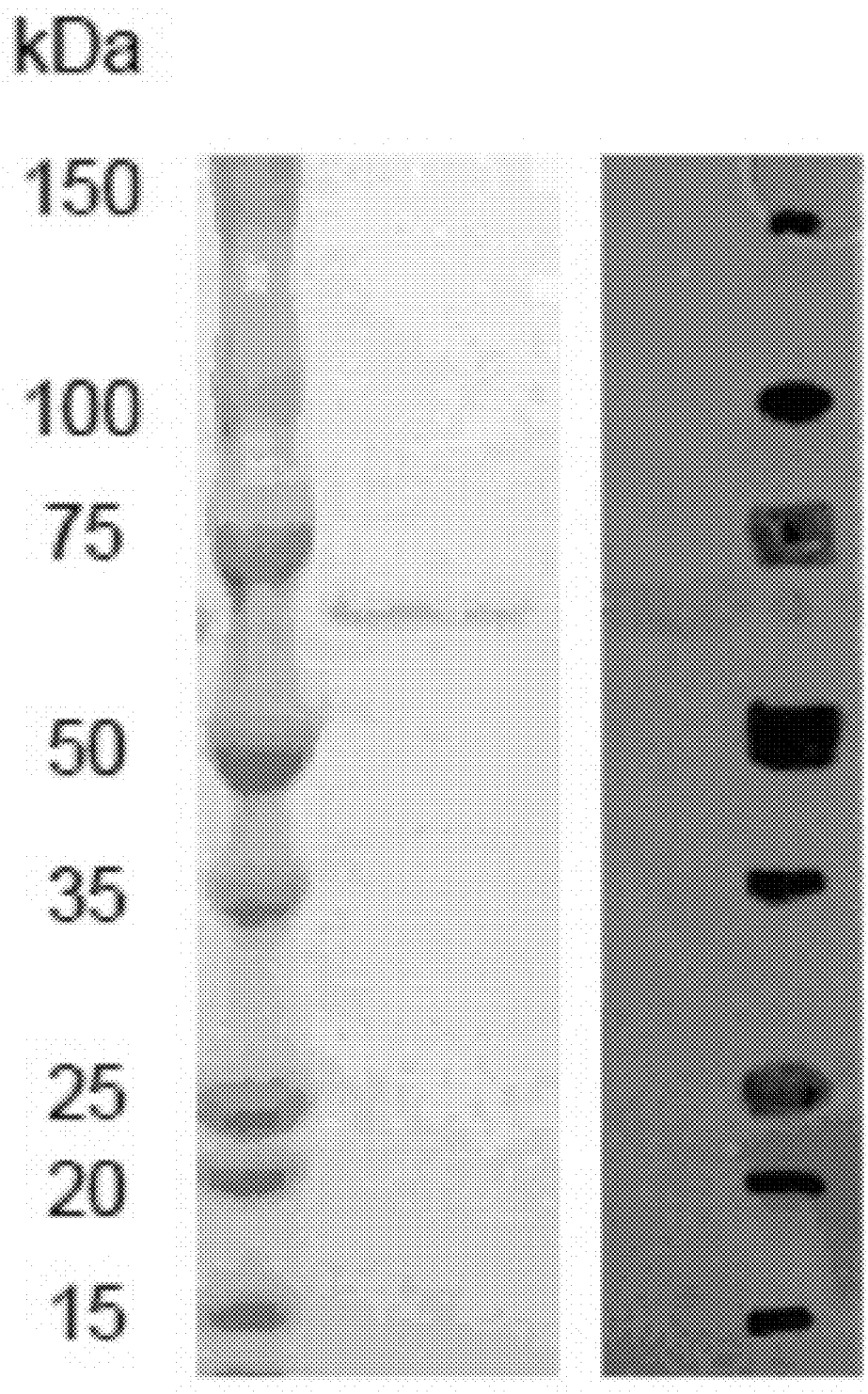
FIG. 2 is a diagram showing SDS-PAGE and activity staining of purified NucL.

A nucleolytic enzyme with a molecular weight of about 66.5 kDa (named Nuclease L; simply referred to as NucL, hereinafter) was purified until the nucleolytic enzyme came to a single band in an electrophoresis manner with the use of hydrophobicity (butyl-Toyopearl and phenyl-Sepharose), and heparin affinity chromatography (See FIG. 2). The summary of purification is shown in Table 2.

TABLE 2

|  | Total amount of protein (mg) | Total amount of activity (U) | Specific activity (U/mg) | Yield (%) |
|---|---|---|---|---|
| Culture supernatant | 3897.9 | 25039145 | 6425 | 100 |
| Butyl-Toyopearl 650M | 73.3 | 1371407 | 18700 | 5.5 |
| Phenyl-Sepharose | 11.4 | 584843 | 51235 | 2.3 |
| Heparin FF | 0.5 | 25551 | 56337 | 0.1 |

The specific activity of NucL was $5.6 \times 10^4$ U/mg-protein at 37 degrees Celsius in 20 mM of Tris/HCl at pH 8.5 that contains 1 mM of $MgCl_2$ and 1 mM of $CaCl_2$. The isoelectric point was measured by using Novex (Registered Trademark) IEF pH-3-10 gel (manufactured by Invitrogen); and then pI was 7.0. Then, it was determined that a N-terminal amino acid sequence of the purified enzyme was DSVRIHDIQGTTR. The sequence matched 12 out of 13 amino acids of putative protein (putative secreted hydrolase) coded on a genome of *Streptomyces scabiei* 87.22, and of putative protein (large secreted protein) coded on a genome of *S. avermitilis* MA-4680.

Furthermore, tryptic digestion of the purified enzyme was carried out after SDS-PAGE, and the purified enzyme was then subjected to LC-MS/MS analysis. As a result, eight short amino acid sequences (6 to 21 amino acids) that matched the following amino acid sequences were detected in total: the amino acid sequences of two putative proteins, large secreted protein [derived from *Streptomyces griseoflavus* Tu4000] (Accession number ZP_05541988) and large secreted protein [derived from *Streptomyces avermitilis* MA-4680] (Accession number NP_827523), which are coded on genome sequences of *Streptomyces avermitilis* MA-4680 and *Streptomyces griseoflavus* Tu4000. Then, an amino acid sequence of large secreted protein [derived from *Streptomyces avermitilis* MA-4680](Accession number NP_827523) was used to carry out homology search with BLASTP programs. As a result, the amino acid sequence showed about 80 percent homology to: large secreted protein [*Streptomyces sviceus* ATCC 29083] (Accession number ZP_06916237), large secreted protein [derived from *Streptomyces viridochromogenes* DSM 40736] (Accession number ZP_05530648), putative hydrolase [derived from *Streptomyces scabiei* 87.22] (Accession number YP_003492557), large secreted protein [derived from *Streptomyces coelicolor* A3 (2)] (Accession number NP_626174), large secreted protein [derived from *Streptomyces ghanaensis* ATCC 14672] (Accession number ZP_04688952), and large secreted protein [derived from *Streptomyces griseoflavus* Tu4000] (Accession number ZP_05541988). Amino acid sequences of the above proteins were acquired from the NCBI database, and alignment was conducted with the use of software GENETYX (Registered Trademark)—MAC Version 12.1.0. Based on the present alignment amino acid sequence, a highly conserved region was selected, and a primer set G (SEQ ID NO. 19 and No. 20 of the sequence list) was prepared. The entire DNA of MBE174 was used as a template to obtain about 1.6 kb of amplified DNA fragment sequences through PCR with the use of the primer set G, and base sequences were analyzed. Based on the obtained base sequences, a primer set H R (SEQ ID NO. 21 of the sequence list) was designed. Meanwhile, the following base sequences were acquired from the NCBI database: a base sequence 1000 bp that exists in an upstream region of a base sequence that codes large secreted protein [derived from *Streptomyces griseoflavus* Tu4000] (Accession number ZP_05541988); and a base sequence 1000 bp that exists in an upstream region of a base sequence that codes large secreted protein [derived from *Streptomyces coelicolor* A3 (2)] (Accession number NP 626174). Based on sequences conserved therein, a primer set H F (SEQ ID NO. 22 of the sequence list) was prepared. The entire DNA of MBE174 was used as a template to obtain about 0.5 kb of amplified DNA fragments through PCR with the use of a primer set H, which is a combination of the primer set H R and the primer set H F. Then, base sequences were analyzed, and a 5'-terminal sequence of nucL gene was obtained. Meanwhile, the entire DNA of MBE174 was digested by restriction enzyme PstI, and a PstI cassette, which was contained in TaKaRa LA PCR in vitro Cloning Kit (manufactured by TAKARA BIO; Cat no. RR015), was connected. The DNA mixture was used as a template to be subjected to PCR reaction with the use of a primer set I (SEQ ID NO. 23 and No. 24 of the sequence list). The obtained PCR reactant was used as a template, and a primer set J(SEQ ID NO. 25 and No. 26 of the sequence list), was also used to acquire about 1.3 kb of amplified fragments. A 3'-terminal base sequence of nucL gene was analyzed. All the base sequences of DNA amplified fragments that were obtained through PCR with the use of the above-mentioned primer sets G to J were assembled to determine an entire-length base sequence (SEQ ID NO. 6 of the sequence list) of nucL gene. Among those closest to the gene sequence of the present enzyme, the gene sequence matched 84 percent (1587/1872 bases) of a region that codes putative large secreted protein of a genome sequence of *S. coelicolor* A3 (2), and 81 percent (1508/1859 bases) of a region that codes putative large secreted protein on a genome of *S. avermitilis* MA-4680. Moreover, among those closest to the amino acid sequence (SEQ ID NO. 4 of the sequence list) that the present gene codes, the amino acid sequence matched 80 percent (491/613 amino acids) of putative large secreted protein that is coded on a genome of *S. coelicolor* A3 (2), and 80 percent (488/609 amino acids) of large secreted protein that is coded on a genome of *S. ghanaensis* ATCC14672. As a result of searching directed to all the genes and proteins registered in the database, the base sequences that showed homology to the present gene were detected. However, there was no protein that was subjected to functional and enzymological analysis after isolation and purification, and had an example of report. Therefore, it is presumed that the NucL protein and the nucL gene have not been reported yet, and are new ones.

Among all the amino acid sequences (607 amino acids) that nucL coded, a sequence from which N-terminal signal peptide was cut was regarded as NucL mature protein (575 amino acids) (SEQ ID NO. 2 of the sequence list). As a result of homology search on Non-redundant protein database with the use of National Center for Biotechnology Information (NCBI, http://www.ncbi.nlm.nih.gov/), BLASTP programs 2.2.24+, the NucL mature protein matched 81 percent (465/574 amino acids) of (putative) large secreted proteins of *Streptomyces coelicolor* A3 (2) and *Streptomyces lividans* TK24; and 80 percent (467/577 amino acids) of large secreted protein of *Streptomyces ghanaensis* ATCC 14672.

5. Biochemical Properties of NucS and NucL

The following shows test results of biochemical properties of NucS and NucL.

(1) Effects of pH on Enzyme Activity

Figure 3:
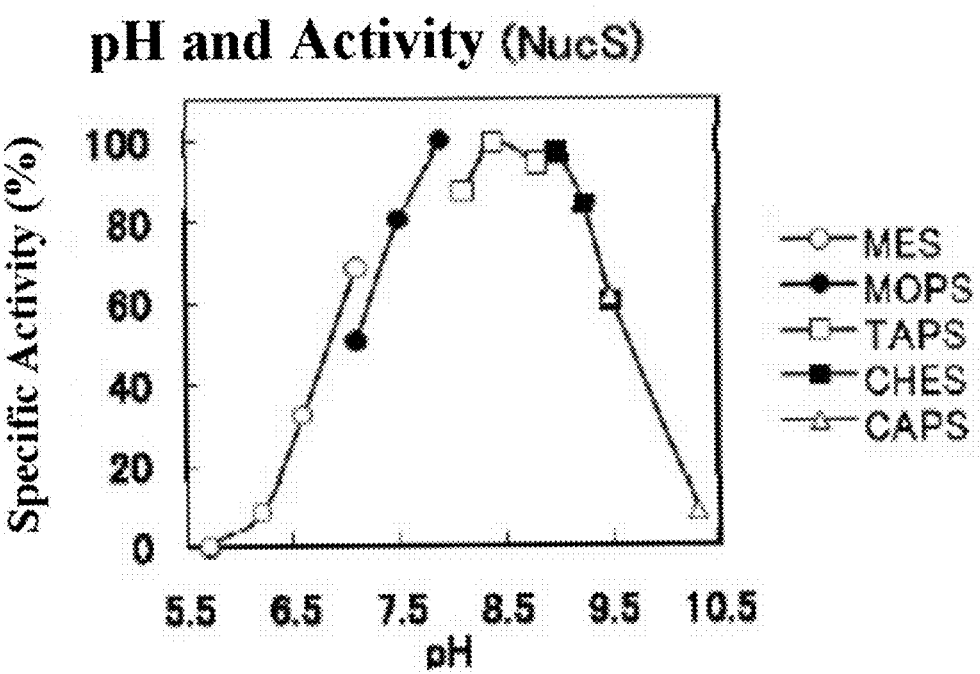
FIG. 3 is a diagram showing the relationship between pH and activity of NucS.
Figure 4:
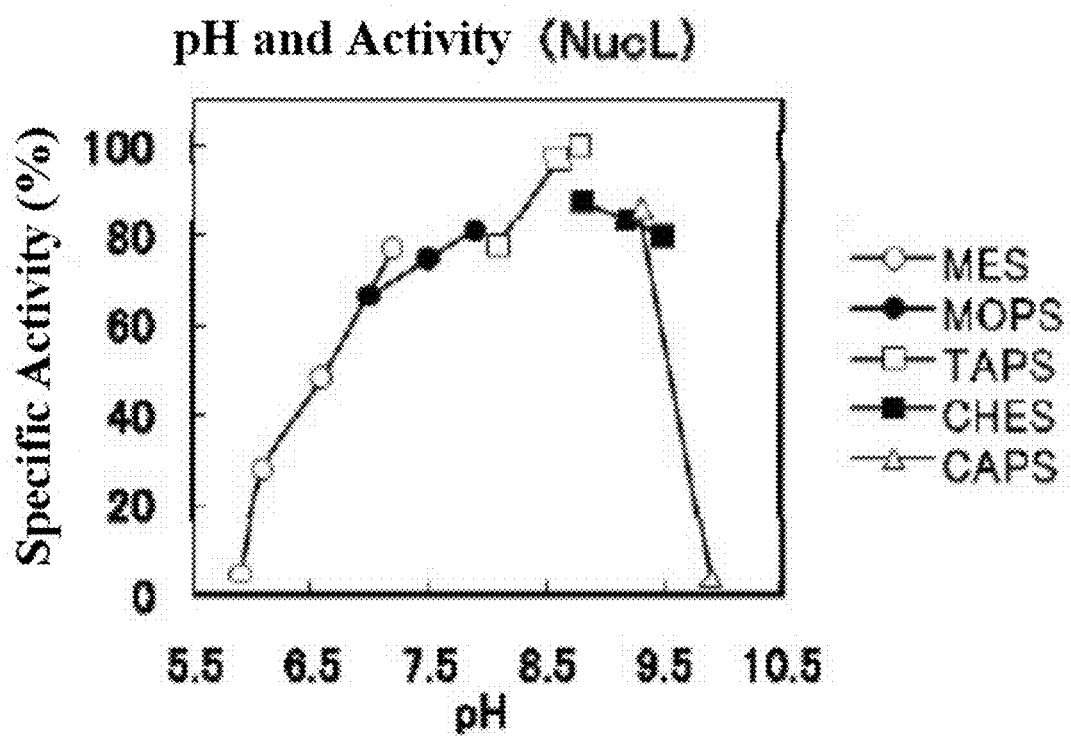
FIG. 4 is a diagram showing the relationship between pH and activity of NucL.

At each level of pH, the nucleic-acid degradation activity was measured at 25 degrees Celsius for 15 minutes by using, as substrate, Deoxyribonucleic acid sodium salt from salmon testes 0.4 mg/mL (manufactured by Sigma-Aldrich; Cat no. D1626-1G) in 20 mM of the following solution containing 1 mM of $MgCl_2$ and 1 mM of $CaCl_2$: 2-morpholino ethane-sulfonic acid; monohydrate/NaOH(MES, pH 5.5 to 7.0); 3-morpholino propanesulfonic acid/NaOH (MOPS, pH 7 to 8); N-tris(hydroxymethyl)methyl-3-aminopropanesulfonic acid/NaOH (TAPS, pH 8 to 9); N-cyclohexyl-2-aminoethanesulfonic acid/NaOH (CHES, pH 9 to 9.5); or N-cyclohexyl-3-aminopropanesulfonic acid/NaOH (CAPS, 9.5 to 10). It was found that the optimum reaction pH of NucS was around 8.5, and the optimum reaction pH of NucL was around 8.8 (referring to FIGS. 3 and 4).

(2) Effects of Temperature on Enzyme Activity

Figure 5:
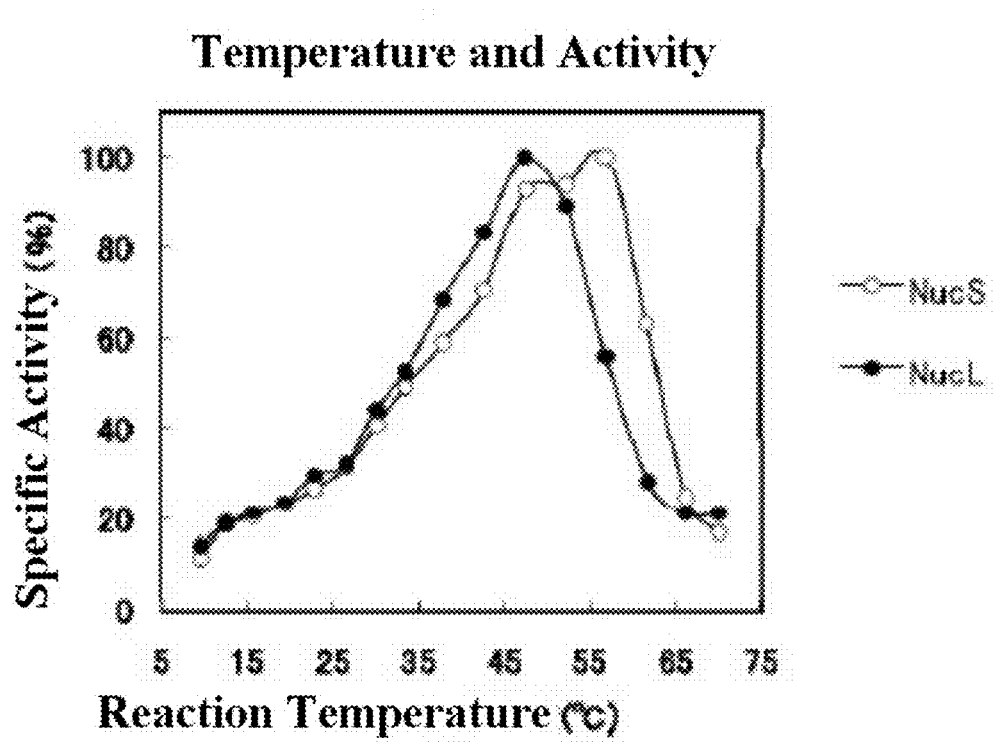
FIG. 5 is a diagram showing the relationships between temperature and activity of NucS and NucL.

Under each temperature condition, the nucleic-acid degradation activity was measured for 15 minutes in 20 mM of Tris/HCl at pH 8.5 that contained 1 mM of $MgCl_2$ and 1 mM of $CaCl_2$. It was found that the optimum reaction temperature of NucS was around 55 degrees Celsius, and the optimum reaction temperature of NucL was around 45 degrees Celsius (referring to FIG. 5).

(3) Thermal Stability Test

Figure 6:
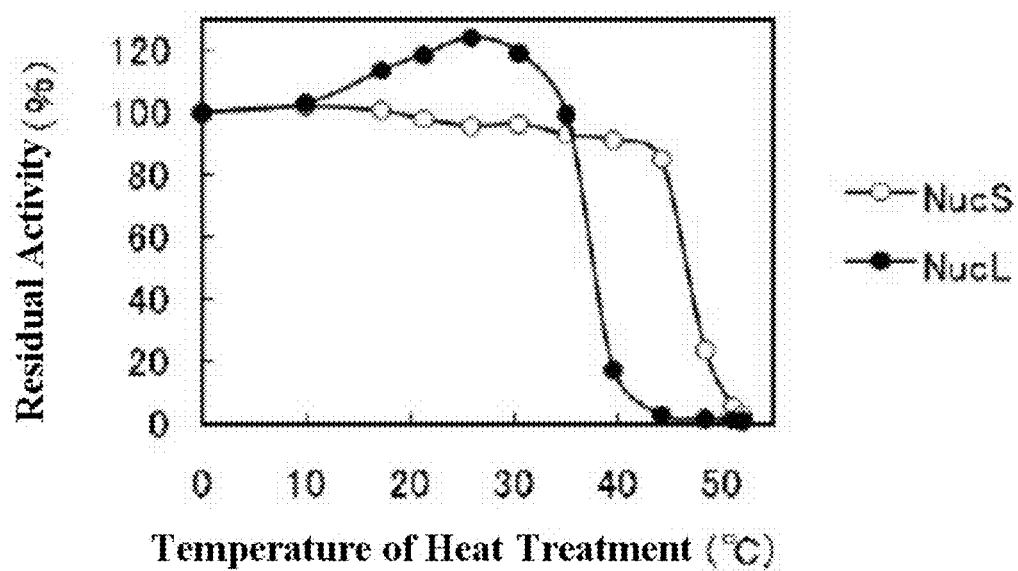
FIG. 6 is a diagram showing results of a thermal stability test of NucS and NucL.

After heat treatment was conducted for 30 minutes at each temperature in 20 mM of Tris/HCl at pH 8.5 that contained 1 mM of $MgCl_2$ and 1 mM of $CaCl_2$, the residual activity was measured (referring to FIG. 6). An activity of an enzyme stored in an ice bath was regarded as 100 percent. As a result, it was found that NucS remained stable until the temperature reached 45 degrees Celsius, and NucL remained stable until the temperature reached 35 degrees Celsius.

(4) Effects of Monovalent Salt on Enzyme Activity

Figure 7:
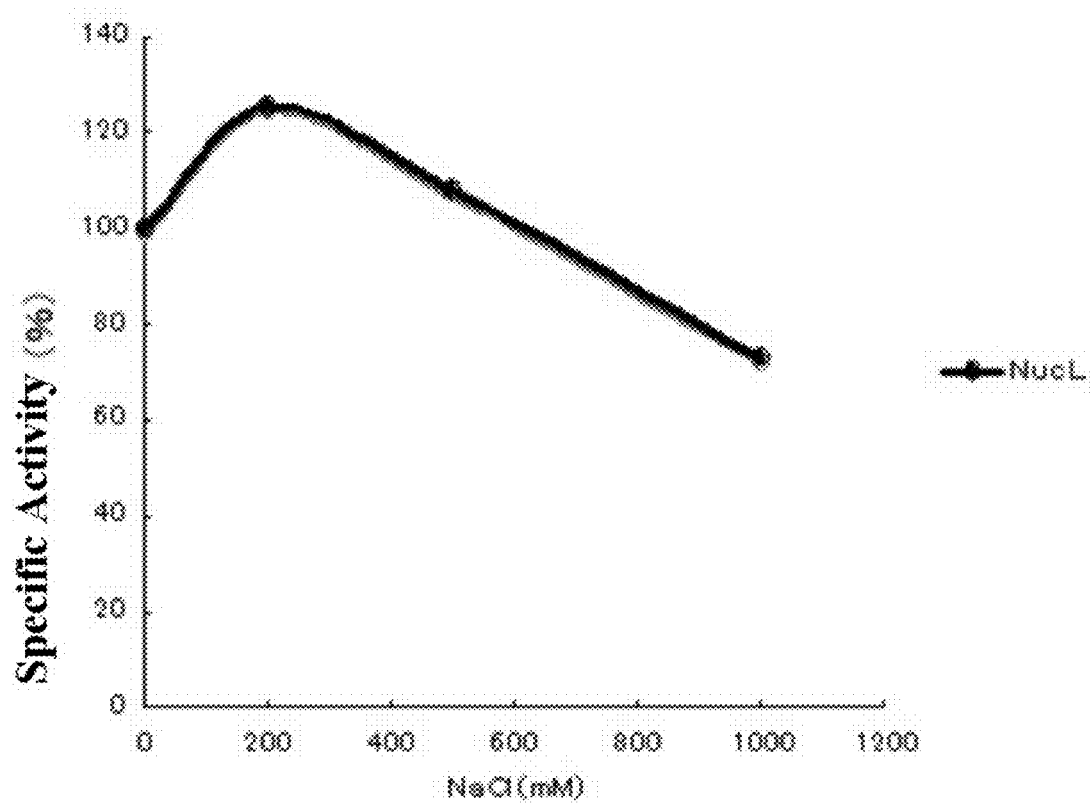
FIG. 7 is a diagram showing effects of monovalent salt (NaCl) on enzyme activity of NucL.
Figure 8:
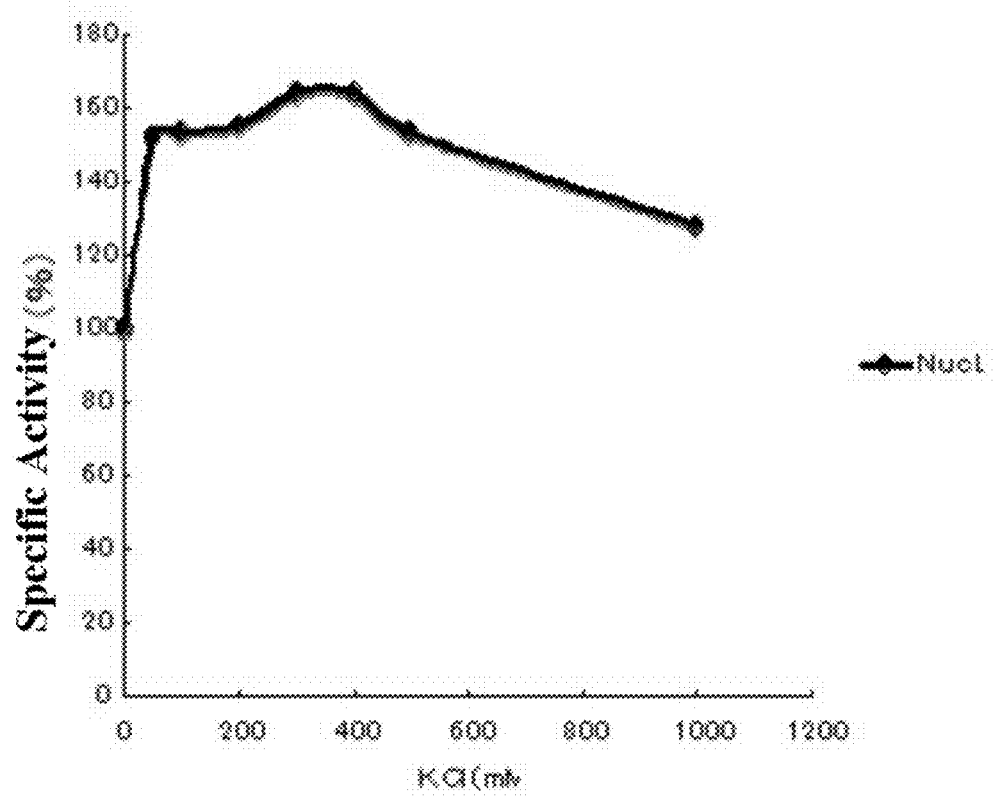
FIG. 8 is a diagram showing effects of monovalent salt (KCl) on enzyme activity of NucL.

Effects of monovalent salt on NucS and NucL were examined. At each concentration level of NaCl, the nucleic-acid degradation activity was measured at 25 degrees Celsius for 15 minutes by using, as substrate, Deoxyribonucleic acid sodium salt from salmon testes 0.4 mg/mL (manufactured by Sigma-Aldrich; Cat no. D1626-1G) in 10 mM of Tris/HCl at pH 8.5 that contained 1 mM of $MgCl_2$ and 0 to 1,000 mM of NaCl. It was found that the activity of NucS was high when the concentration of NaCl was low, and that NucL remained active even under the condition that NaCl existed in concentration of up to 1,000 mM (referring to FIG. 7). Substantially similar results were obtained even in the case of using KCl (referring to FIG. 8).

(5) Effects of Divalent Metal Salt on Enzyme Activity

Figure 9:
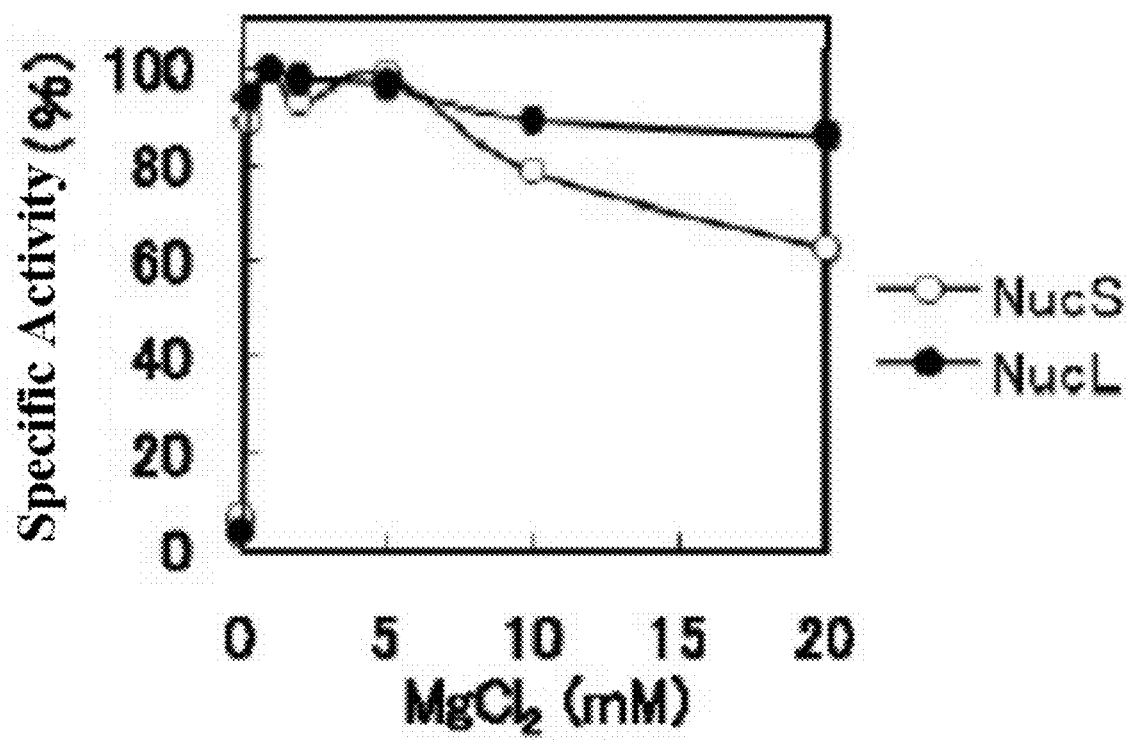
FIG. 9 is a diagram showing effects of divalent metal salt ($MgCl_2$) on enzyme activities of NucS and NucL.
Figure 10:
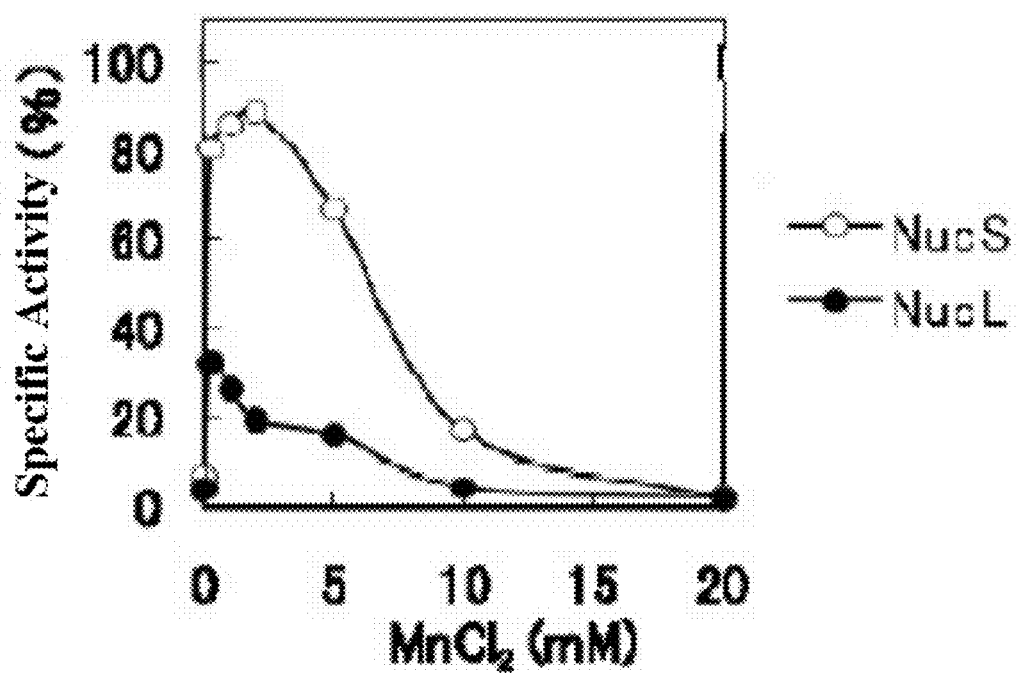
FIG. 10 is a diagram showing effects of divalent metal salt ($MnCl_2$) on enzyme activities of NucS and NucL.

Effects of divalent metal salt on NucS and NucL were examined. NucS or NucL was added to a reaction solution that was obtained by adding, as substrate, Deoxyribonucleic acid sodium salt from salmon testes 0.4 mg/mL (manufactured by Sigma-Aldrich; Cat no. D1626-1G) into 20 mM of Tris/HCl at pH 8.5 that contained 1 mM of $CaCl_2$ and 0 to 20 mM of $MgCl_2$ or $MnCl_2$; and the mixture was incubated in ice for 30 minutes. Then, the nucleic-acid degradation activity was measured at 25 degrees Celsius for 15 minutes. NucS and NucL required divalent metal salt for activation. NucS and NucL showed high levels of activity in the presence of 0.25 to 5 mM of $MgCl_2$ (referring to FIG. 9). Whereas, NucS showed substantially the same level of activity in the presence of 1 to 2 mM of $MnCl_2$ as in the presence of $MgCl_2$ (referring to FIG. 10). Incidentally, in the present test, in order to enhance the stability of the enzymes, 1 mM of $CaCl_2$ was added to all the reaction solutions.

(6) Effects of Phosphate on Enzyme Activity

Figure 11:
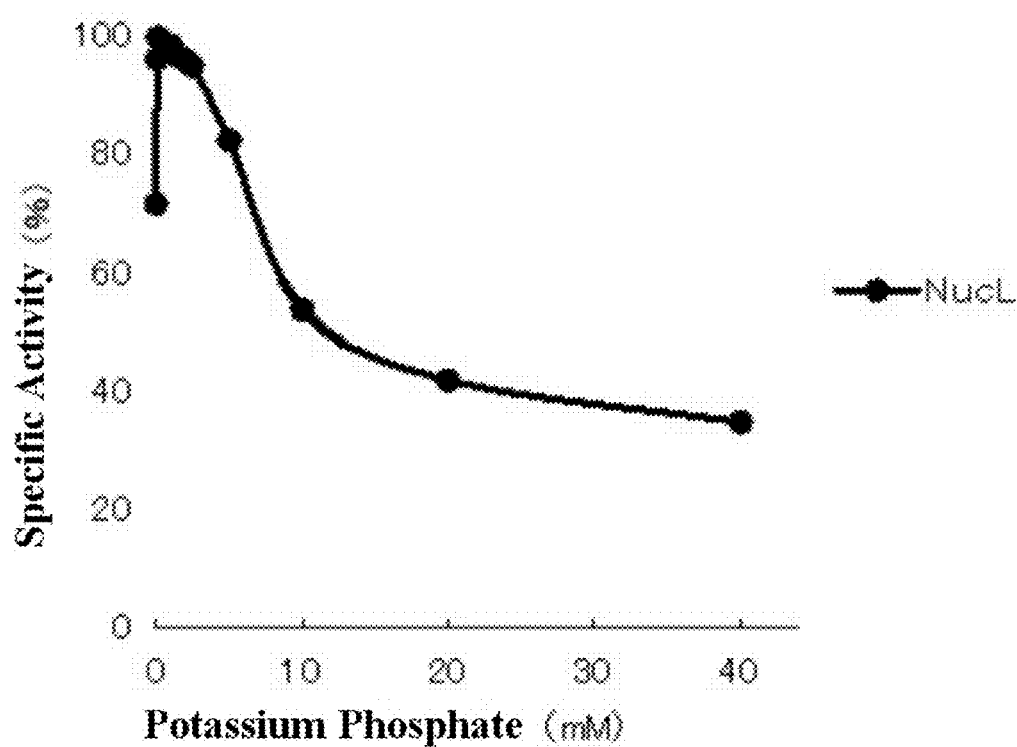
FIG. 11 is a diagram showing effects of phosphate on enzyme activity of NucL.

Effects of phosphate on NucS and NucL were examined. In 0 to 40 mM of potassium phosphate buffer at pH 8.5 that contained 1 mM of $MgCl_2$ and 1 mM of $CaCl_2$, the nucleic-acid degradation activity was measured at 25 degrees Celsius for 15 minutes by using, as substrate, Deoxyribonucleic acid sodium salt from salmon testes 0.4 mg/mL (manufactured by Sigma-Aldrich; Cat no. D1626-1G). It was found that NucS was strongly inhibited by phosphate, and that 0.5 mM or more of phosphate made NucS inactive. Meanwhile, compared with NucS, NucL was excellent in resistance to phosphate. NucL could maintain 50 percent of activity even in the presence of 10 mM of potassium phosphate (referring to FIG. 11).

(7) Effects of Various Chemical Substances on Enzyme Activity

NucS and NucL were kept in contact with the compounds listed in Table 3 on an ice bath for one hour, and then, the enzyme activity was measured by the standard specific activity measurement method (referring to Table 3). As shown in Table 3, NucS and NucL were strongly inhibited by $ZnCl_2$, $CuCl_2$, and EDTA. Meanwhile, NucS showed high resistance to dimethyl sulfoxide and dimethyl formamide. NucL showed high resistance to SDS. Incidentally, poorly water-soluble compounds were dissolved in dimethyl sulfoxide, and then added to an enzyme solution. The final concentration of dimethyl sulfoxide after addition was 5 percent. The activity in the presence of 5 percent of dimethyl sulfoxide was regarded as being 100 percent.

TABLE 3

| Chemical substances | Concentration | Relative activity of NucS (%) | Relative activity of NucL (%) |
|---|---|---|---|
| $ZnCl_2$ | 0.1 mM | 3 | 1 |
| | 1.0 mM | 0 | 0 |
| $CuCl_2$ | 0.1 mM | 111 | 96 |
| | 1.0 mM | 3 | 9 |
| Ethylenediaminetetraacetic acid | 5.0 mM | 0 | 0 |
| | 10.0 mM | 0 | 0 |
| Melcaptoethanol | 1.0 mM | 112 | 89 |
| | 5.0 mM | 116 | 92 |
| Dithiothreitol | 1.0 mM | 105 | 89 |
| | 5.0 mM | 104 | 89 |
| Iodoacetic acid | 0.1 mM | 103 | 102 |
| | 1.0 mM | 96 | 97 |
| Parachloro mercury benzoate | 0.1 mM | 92 | 108 |
| | 1.0 mM | 94 | 91 |
| Phenylmethanesulfonyl fluoride | 1.0 mM | 85 | 111 |
| | 5.0 mM | 87 | 99 |
| Dimethyl sulfoxide | 1.0% | 110 | 105 |
| | 10.0% | 116 | 75 |
| | 20.0% | 113 | 40 |
| Dimethyl formamide | 1.0% | 91 | 99 |
| | 10.0% | 118 | 74 |
| | 20.0% | 117 | 56 |
| SDS | 0.1% | 85 | 89 |
| | 1.0% | 0 | 121 |
| Triton X | 0.1% | 115 | 137 |
| | 1.0% | 108 | 128 |
| Urea | 2.0M | 125 | 64 |
| | 4.0M | 126 | 55 |
| | 6.0M | 92 | 43 |
| Additive-free | — | 100 | 100 |

Figure 12:
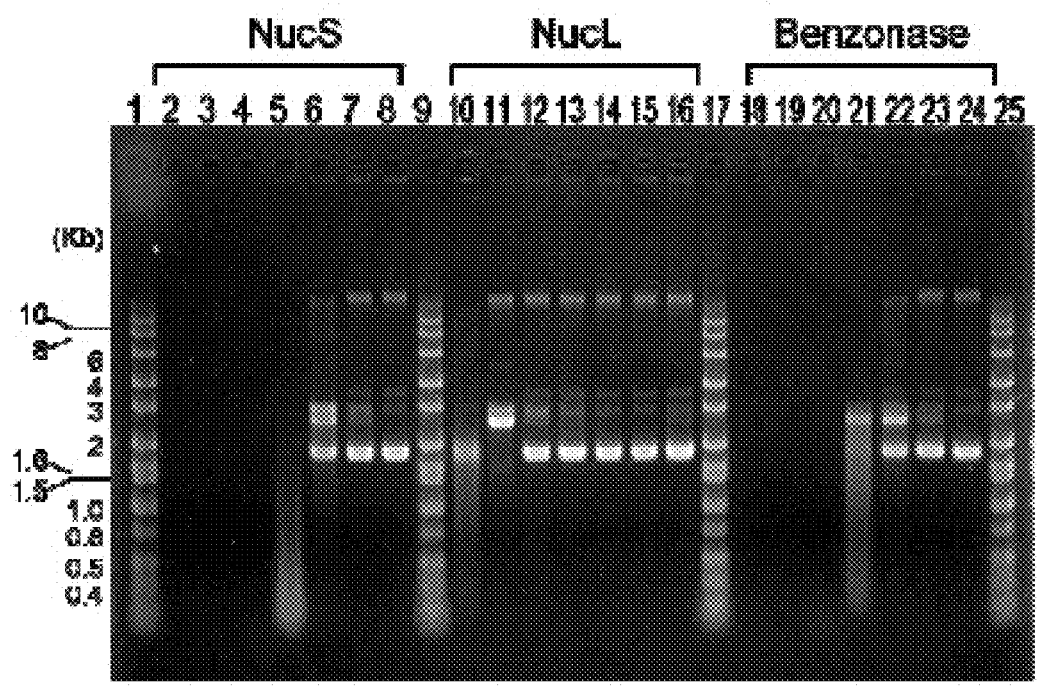
FIG. 12 is a diagram showing results of analysis on degradation manners of NucS, NucL, and Benzonase for circular plasmid DNA.

6. Pattern of Nucleic-Acid Degradation by NucS and NucL and Substrate Specificity (1) Analysis of Degradation Styles for Circular Plasmid DNA of NucS and NucL Circular plasmid DNA (pUC 18) that had been purified by using a plasmid purification kit (HiSpeed (Registered Trademark) Plasmid Midi Kit; manufactured by QIAGEN, Cat no. 12643) was used as substrate to analyze nucleic-acid degradation styles of NucS and NucL. According to the standard specific activity measurement method, the enzyme solutions that were different in enzyme level as shown in the table below were added to a plasmid solution (about 2 to 10 μg). Then, a nucleic-acid degradation reaction was carried out at 25 degrees Celsius for 15 minutes. After the degradation, a reaction solution was subjected to a 1-percent agarose gel electrophoresis, and the degradation manner of the degraded DNA was analyzed. FIG. 12 shows the appearance of DNA degraded in changing the enzyme concentration (Reaction at 25 degrees Celsius). As a reference, FIG. 12 also shows test results of the case where Benzonase (with the same number of units) was used. Incidentally, the description of each lane is shown in Table 4.

TABLE 4

| | Lane | | | | | | | |
|---|---|---|---|---|---|---|---|---|
| | 2, 10, 18 | 3, 11, 19 | 4, 12, 20 | 5, 13, 21 | 6, 14, 22 | 7, 15, 23 | 8, 16, 24 | 1, 9, 17, 25 |
| Enzyme level (U) | $10^{-1}$ | $10^{-2}$ | $10^{-3}$ | $10^{-4}$ | $10^{-5}$ | $10^{-6}$ | 0 | Size marker |

Figure 13:
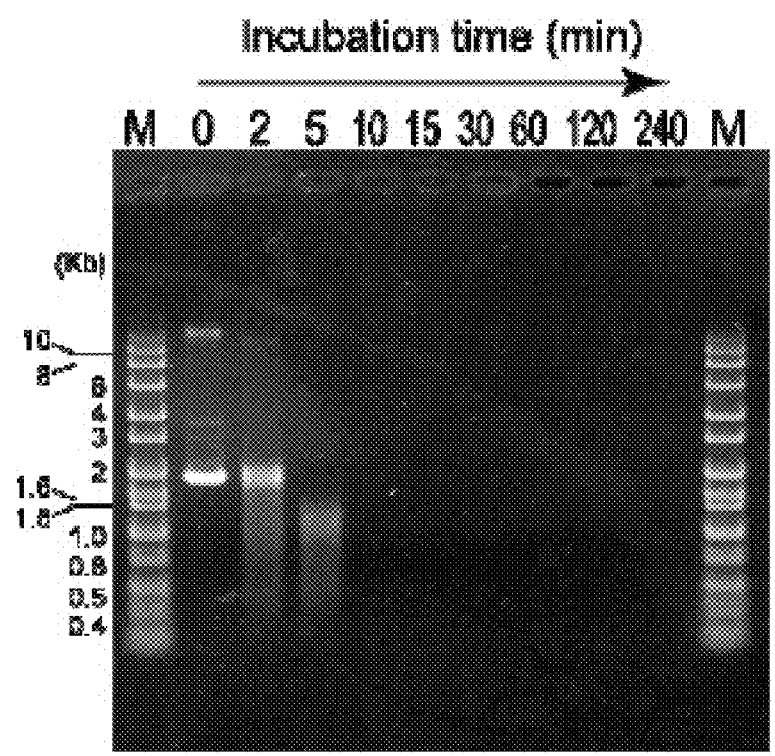
FIG. 13 is a diagram showing results of degradation of circular plasmid DNA by NucL.

Next, the enzyme level of NucL was increased to 0.5 U, and a test was conducted to examine if the plasmid could be completely degraded (referring to FIG. 13). From the above results, it was found that, as for the circular plasmid DNA, NucS and NucL were used as single enzymes and could completely degrade the plasmids regardless of the shape of a supercoiled type or relaxed type.

Figure 14:
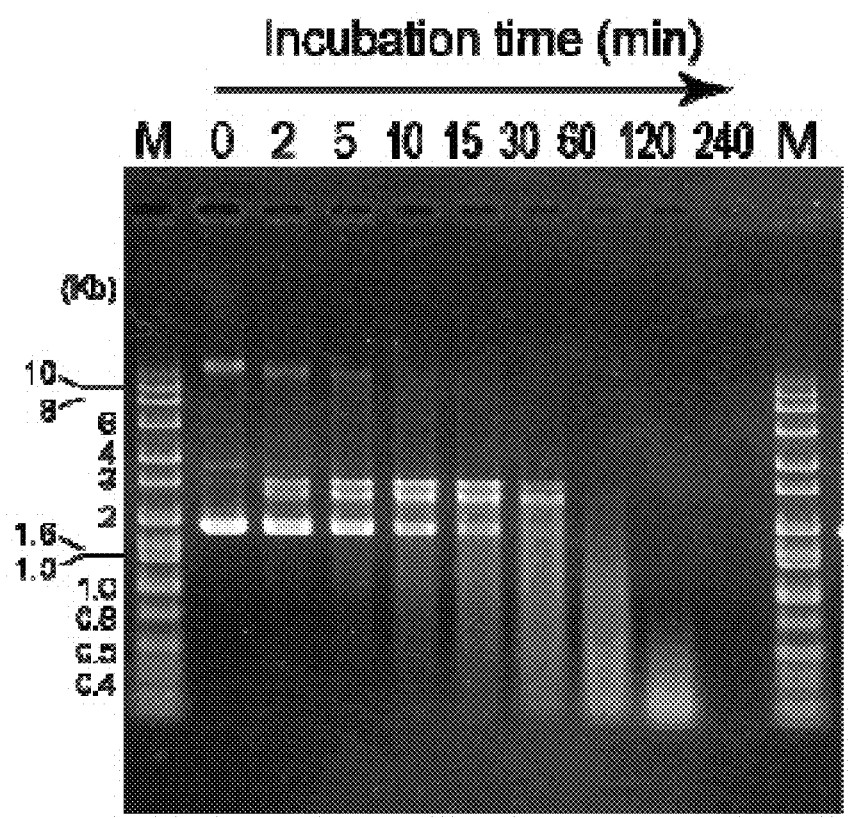
FIG. 14 is a diagram showing reaction results in an initial stage of degradation reaction of circular plasmid DNA by NucS.
Figure 15:
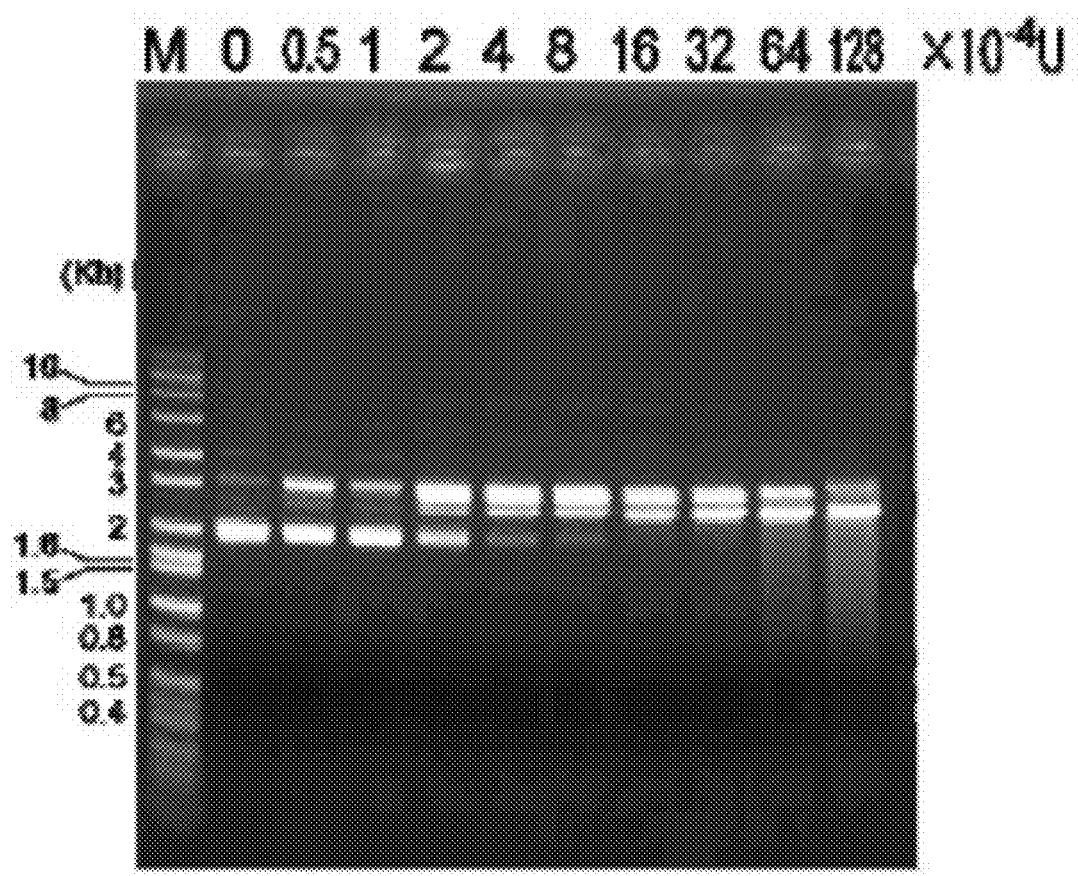
FIG. 15 is a diagram showing reaction results in an initial stage of degradation reaction of circular plasmid DNA by NucL.

(2) Analysis of Reaction Styles in Initial Stage of Degradation Reaction for Circular DNA of NucS and NucL According to the standard specific activity measurement method, reaction styles in an initial stage of degradation reaction for circular DNA (pUC18 plasmid) of NucS and NucL were analyzed (referring to FIGS. 14 and 15). Given the results thereof, it was presumed that NucS has degradation activity of an endo-type style. Moreover, NucL showed a reaction pattern similar to a single strand-specific, endo-type nucleolytic enzyme, which was reported by Desai and Shankar (referring to Eur. J. Biochem. 267, 5123-5135, 2000; the contents of the document are incorporated herein by reference). The degradation of circular plasmid DNA executed by the single strand-specific nucleolytic enzyme is considered to proceed as the molecular weight degreases due to accumulation of endo-type cleavage of single strands.

(3) Degradation Pattern of Linear Double-Stranded DNA

Figure 16:
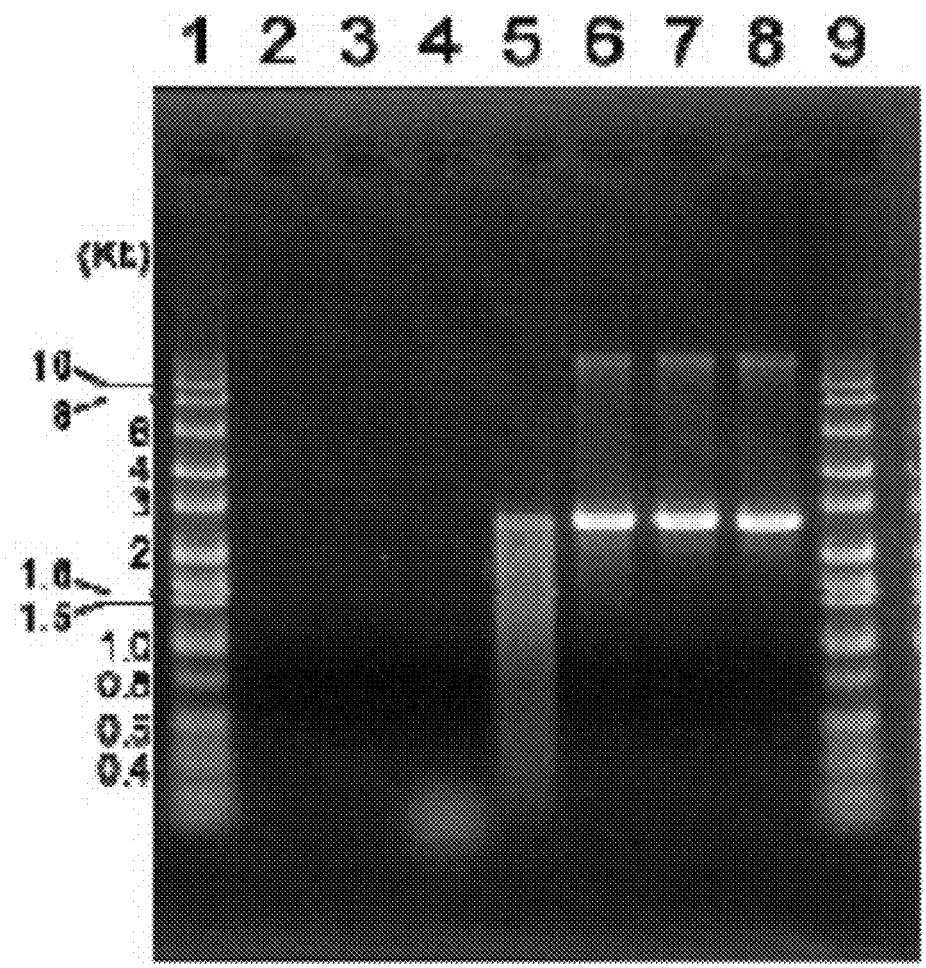
FIG. 16 is a diagram showing results of degradation of linear double-stranded DNA by NucS.
Figure 17:
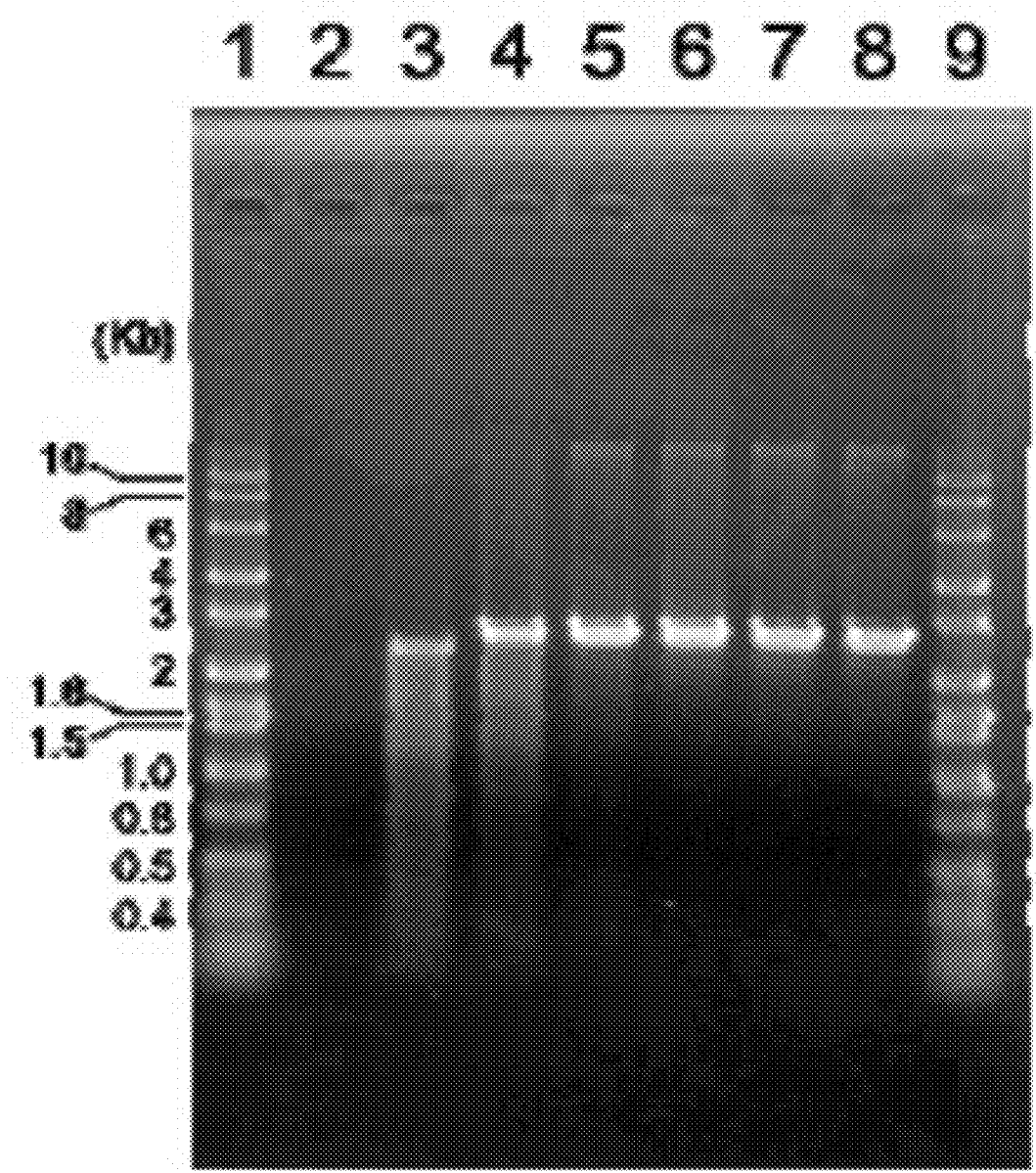
FIG. 17 is a diagram showing results of degradation of linear double-stranded DNA by NucL.

With the use of the standard specific activity measurement method, as well as of a substrate obtained by making circular DNA (pUC18 plasmid) linear by using restriction nucleases BamHI (which generates a 5'-protruding end), SacI (which generates a 3'-protruding end), and SmaI (which generates a flush end), a degradation reaction took place with the use of NucS and NucL (referring to FIGS. 16 and 17). Incidentally, the description of each lane is shown in Table 5.

TABLE 5

| | Lane | | | | | | | |
|---|---|---|---|---|---|---|---|---|
| | 2 | 3 | 4 | 5 | 6 | 7 | 8 | 1, 9 |
| Enzyme level (U) | $10^{-1}$ | $10^{-2}$ | $10^{-3}$ | $10^{-4}$ | $10^{-5}$ | $10^{-6}$ | 0 | Size marker |

From the results thereof, it was found that each of NucS and NucL can degrade, as single enzymes, the linear double-stranded DNA regardless of the structure of DNA strand ends. As a result of comparison of FIGS. 12 and 16 with FIG. 17, it was also found that NucS degrades the circular DNA and the linear double-stranded DNA at the same level of efficiency. Meanwhile, NucL degraded the linear double-stranded DNA more efficiently than the circular DNA. Furthermore, the maximum size of DNA, which was observed in the middle of the reaction and whose degradation did not proceed, remained constant from the start of the reaction in the case of NucS (main bands of lanes 5 to 8 shown in FIG. 16); in the case of NucL, a decrease in the size occurred (Comparison of the main bands of lane 3 with the main bands of lanes 4 to 8 shown in FIG. 17). The finding suggests that the degradation of DNA executed by NucL took place more efficiently rather in terminal portions than in random positions, i.e. that an exo-type degradation reaction proceeded. Given the above results, it is presumed that NucL has a reaction style called an endo-exo type.

(4) Reactivity Test for Single-Stranded DNA, Double-Stranded DNA, and RNA

With the use of a 15-minute standard specific activity measurement method, the reactivity of each enzyme was tested for salmon DNA (double-stranded DNA) that was dissolved at low temperatures, as well as for the same DNA (single-stranded DNA) that had been subjected to thermal denaturation at 95 degrees Celsius for 10 minutes. As a result, it was found that NucS degrades the native DNA and the thermally-denatured DNA at the same level of efficiency; and that the level of efficiency at which NucL degraded the thermally-denatured DNA was about five times higher than the level of efficiency at which NucL degraded the native DNA. That is, it can be said that NucL is an enzyme that efficiently works on single-stranded DNA. Furthermore, as a result of measuring the degrading activity for RNA (mRNA derived from yeast), NucS showed RNA degrading activity. However, NucL did not show RNA degrading activity.

(5) Activity Test of Phosphodiesterase and Phosphatase

Bis(p-nitrophenyl)phosphate and p-nitrophenylphosphate were used as substrate. The method of Tomoyeda et al. (referring to Archives of biochemistry and biophysics. 131(1), 191-202, 1969; the contents of the document are incorporated herein by reference) was used. In 100 mM of Tris/HCl at pH 8.5 that contained 1 mM of $MgCl_2$, 1 mM of $CaCl_2$, and 1 percent of glycerol, with the use of a reaction solution that contained 0.2 percent of the above substrate, the phosphodiesterase activity and phosphatase activity of both enzymes were measured at 25 degrees Celsius. As a result, it was found that NucS does not have phosphodiesterase or phosphatase activities. However, it was found that NucL has both phosphodiesterase and phosphatase activities.

7. Summary

NucS has a significantly higher specific activity than a commercially available nucleolytic enzyme, and can efficiently degrade various nucleic acids (linear and circular single-stranded and a double-stranded type DNAs and RNAs) in an endo type manner under conditions of low salt concentration. NucL degrades DNAs (linear and circular single-stranded and a double-stranded type DNAs) in an endo-exo type manner under conditions of a wide range of salt concentration. Accordingly, it is expected that the combined use of NucS and NucL can achieve an excellent nucleic-acid degradation activity under wide-range conditions. Both enzymes show high levels of activity in the presence of a low-concentration level (1 mM) of $Mg^{2+}$ and $Ca^{2+}$ without requiring addition of $Mn^{2+}$. Moreover, the bacteria that produce the present enzymes are bacteria of the genus *Streptomyces*, which are easily cultured and considered to be remarkably safe. Therefore, the enzymes can be considered to be favorable candidates for nucleic-acid degradation industrial-use enzymes used in a process of producing food and medicine. By culturing nucleolytic enzyme high-producing actinomycete *Streptomyces* sp. MBE174, and by using a novel gene that codes the present enzyme, it is considered that nucleolytic enzymes can be provided at low cost.

Sequences disclosed in the sequence list are as follows:

```
No. 1 Core sequence of NucS:
ALPTPVSAATARGYLASLKVAPENRTGYKRDLFPHWITQSGTCNTRETVLKRDGTNVVTDAA

CAATSGSWYSPFDGATWTAASDVDIDHLVPLAEAWDSGASAWTTAQRQAFANDLTRPQLLAV

TDTVNQSKGDKDPAEWMPPRAAYHCTYVRAWVQ;

No. 2 NucL mature protein:
DSVRIHDIQGTTRISPYAGRQVADVPGVVTGVRDHGSSRGFWFQDPRPDDDPATSEGVFVFT

GSAPGVEAGDAVTVSGTVSEFVPGGTASGNQSLTEITRPTVTVVSRGNPVPDPVVVSARSVP

HAYAPAGDAAANGSVNALPLRPDRYALDYYESLEGMNVQVADARVVGATDPYTELWVTVKPG

ENASPRGGTVYGSRDAQNTGRLQIQTLGVPAGFPAADVGDTLAGATTGPLDYNQFGGYTLVA

RSLGTLTAGGLARETTREQHRDELSVATYNVENLDPSDGTFAAHAEAIVRNLRSPDIVSLEE

IQDDNGATDDGTVTAGVTVGKLIDAVVAAGGPRYDWRSVDPVDKADGGQPGGNIRQVFLFDP

RRVSFADRPGGDAVTATGVVKVRGKAALTHSPGRVDPANPAWLNSRKPLAGEFSFRGRTVFV

IANHFASKGGDQGLTSQYQPPARSSETQRHLQATAVNTFVKQILAVQKNADVIALGDINDFE

FSGTTERLEAGGALWSAVRSLPPGGERYSYVYQGNSQVLDQILVSPSIRRGHLSYDSVHINAE

FHDQISDHDPQVLRYRP;
```

-continued

No. 3 NucS:
MPKLYARRRFAVLAALTGLIASAGLFHGPAASAALPTPVSAATARGYLASLKVAPENRTGYK

RDLFPHWITQSGTCNTRETVLKRDGTNVVTDAACAATSGSWYSPFDGATWTAASDVDIDHLV

PLAEAWDSGASAWTTAQRQAFANDLTRPQLLAVTDTVNQSKGDKDPAEWMPPRAAYHCTYVR

AWVQVKYYYGLSVDTAEKTALTNRLAGC;

No. 4 NucL:
MASQSVTRLAALTVAATCSAASVVVLGPPAHADSVRIHDIQGTTRISPYAGRQVADVPGVVT

GVRDHGSSRGFWFQDPRPDDDPATSEGVFVFTGSAPGVEAGDAVTVSGTVSEFVPGGTASGN

QSLTEITRPTVTVVSRGNPVPDPVVVSARSVPHAYAPAGDAAANGSVNALPLRPDRYALDYY

ESLEGMNVQVADARVVGATDPYTELWVTVKPGENASPRGGTVYGSRDAQNTGRLQIQTLGVP

AGFPAADVGDTLAGATTGPLDYNQFGGYTLVARSLGTLTAGGLARETTREQHRDELSVATYN

VENLDPSDGTFAAHAEAIVRNLRSPDIVSLEEIQDDNGATDDGTVTAGVTVGKLIDAVVAAG

GPRYDWRSVDPVDKADGGQPGGNIRQVFLFDPRRVSFADRPGGDAVTATGVVKVRGKAALTH

SPGRVDPANPAWLNSRKPLAGEFSFRGRTVFVIANHFASKGGDQGLTSQYQPPARSSETQRH

LQATAVNTFVKQILAVQKNADVIALGDINDFEFSGTTERLEAGGALWSAVRSLPPGERYSYV

YQGNSQVLDQILVSPSIRRGHLSYDSVHINAEFHDQISDHDPQVLRYRP;

No. 5 nucS gene:
ATGCCGAAGCTCTACGCGCGTCGACGGTTCGCCGTCCTCGCCGCGCTCACCGGACTCATAGC

CTCCGCCGGGCTCTTCCACGGTCCGGCCGCCTCCGCCGCCCTCCCCACGCCGGTCAGCGCCG

CCACCGCCCGCGGCTACCTCGCCTCCCTGAAGGTGGCCCCCGAGAACCGCACCGGCTACAAG

CGCGACCTCTTCCCCCACTGGATCACGCAGTCCGGCACCTGCAACACCCGCGAGACCGTCCT

CAAACGCGACGGCACCAACGTCGTCACCGACGCCGCCTGCGCCGCCACCAGCGGCAGTTGGT

ACTCGCCCTTCGACGGGGCCACCTGGACCGCCGCCTCCGACGTCGACATCGACCACCTCGTC

CCGCTGGCCGAGGCGTGGGACTCCGGCGCGAGCGCCTGGACCACGGCCCAGCGCCAGGCGTT

CGCCAACGACCTGACACGTCCTCAGCTCCTCGCCGTCACCGACACCGTGAACCAGTCCAAGG

GCGACAAGGACCCGGCCGAGTGGATGCCGCCCCGGGCCGCCTACCACTGCACCTACGTACGC

GCCTGGGTGCAGGTGAAGTACTACTACGGCCTCTCGGTCGACACCGCCGAGAAGACGGCGCT

CACGAACCGGCTCGCCGGCTGCTGA;

No. 6 nucL gene:
TTGGCCAGCCAGTCCGTCACGCGCCTCGCCGCGCTCACCGTCGCCGCCACCTGTTCGGCGGC

GTCCGTCGTCGTCCTCGGTCCGCCCGCGCACGCCGACTCCGTGCGCATCCACGACATCCAGG

GCACCACCAGGATCTCCCCGTACGCCGGCCGCCAGGTCGCCGACGTGCCCGGCGTCGTCACC

GGAGTCCGCGACCACGGCTCCTCCCGGGGCTTCTGGTTCCAGGACCCGCGGCCCGACGACGA

CCCCGCCACCAGCGAGGGAGTGTTCGTCTTCACCGGCTCGGCCCCCGGGGTCGAGGCCGGCG

ACGCGGTCACCGTCTCCGGCACGGTCTCGGAGTTCGTGCCCGGCGGGACCGCCTCCGGCAAC

CAGTCGCTCACCGAGATCACCCGGCCCACGGTCACCGTGGTCTCCCGCGGCAACCCGGTGCC

GGACCCGGTCGTCGTCTCGGCCCGCTCCGTGCCGCACGCCTACGCCCCGGCGGGCGACGCCG

CCGCGAACGGCTCCGTCAACGCCCTGCCCCTGCGGCCCGACCGCTACGCCCTGGACTACTAC

GAGTCCCTGGAGGGCATGAACGTCCAGGTGGCCGACGCCCGCGTGGTCGGCGCGACCGACCC

GTACACCGAGCTGTGGGTGACGGTGAAGCCCGGCGAGAACGCGAGCCCCCGGGGCGGCACCG

TCTACGGCTCCCGCGACGCGCAGAACACCGGGCGGCTGCAGATCCAGACCCTGGGCGTACCA

GCCGGCTTCCCCGCCGCCGACGTGGGCGACACCCTCGCGGGCGCCACCACCGGCCCGCTCGA

-continued
```
CTACAACCAGTTCGGCGGCTACACCCTGGTCGCCCGTAGTCTCGGCACGCTCACCGCCGGCG

GGCTCGCCCGCGAGACGACCCGGGAGCAGCACCGCGACGAGCTGTCGGTGGCCACGTACAAC

GTCGAGAACCTCGACCCCTCCGACGGCACCTTCGCCGCGCACGCGGAGGCGATCGTCCGGAA

CCTGCGCTCACCGGACATCGTGTCCCTGGAGGAGATCCAGGACGACAACGGCGCCACGGACG

ACGGCACGGTGACCGCCGGCGTGACGGTGGGCAAGCTGATCGACGCCGTCGTCGCGGCCGGC

GGCCCGCGCTACGACTGGCGCTCGGTGGACCCCGTCGACAAGGCGGACGGCGGGCAGCCGGG

CGGCAACATCCGCCAGGTGTTCCTCTTCGACCCGCGGCGGGTCTCCTTCGCCGACCGTCCCG

GCGGGGACGCGGTCACCGCGACCGGGGTGGTGAAGGTGCGCGGCAAGGCGGCGCTGACCCAC

TCCCCCGGCCGGGTCGACCCCGCGAACCCCGCCTGGCTGAACAGCCGCAAGCCGCTGGCCGG

CGAGTTCTCGTTCCGCGGGCGGACGGTCTTCGTGATCGCCAACCACTTCGCGTCCAAGGGCG

GCGACCAGGGGCTGACCTCCCAGTACCAGCCGCCGGCGCGGAGTTCGGAGACCCAGCGCCAC

CTCCAGGCGACGGCGGTGAACACCTTCGTCAAGCAGATCCTGGCGGTCCAGAAGAACGCGGA

CGTCATCGCCCTCGGCGACATCAACGACTTCGAGTTCTCCGGCACGACGGAACGCCTGGAGG

CCGGCGGCGCGCTCTGGTCGGCGGTCAGGTCGCTGCCGCCGGGCGAGCGCTACTCGTACGTC

TACCAGGGCAACAGCCAGGTGCTCGACCAGATCCTGGTGAGCCCGTCGATCCGGCGCGGGCA

CCTGTCCTACGACAGCGTGCACATCAACGCCGAGTTCCACGACCAGATCAGCGACCACGACC

CGCAGGTGCTGCGGTACCGCCCCTGA;

No. 7 primer set A F:
CGCATG(C/T)C(A/G)AAG(G/T)TCTACG;

No. 8 primer set A R:
A(A/G)CTGCCGCTGGTGG;

No. 9 primer set B F:
AGCGGCAG(C/T)TGGTACTC;

No. 10 primer set B R:
ACCCGCGATCTGGAAGG;

No. 11 primer set C F:
GCTACAAGCGCGACCTCTTC;

No. 12 primer set C R:
TGGACTGGTTCACGGTGTC;

No. 13 primer set D F:
AACTGCCGCTGGTGG;

No. 14 primer set D R:
CTGAGCAGTATGTCGACGGTC;

No. 15 primer set E F:
GCTACAAGCGCGACCTCTTC;

No. 16 primer set E R:
GTTAGAACGCGTAATACGAC;

No. 17 primer set F F:
CTGGGTGCAGGTGAAGTACTAC;

No. 18 primer set F R:
GTAATACGACTCACTATAGG;

No. 19 primer set G F:
GGCTTCTGGAT(A/G/C)CAGGACCC;

No. 20 primer set G R:
CTGCGGGTCGTGGTCG;

No. 21 primer set H R:
CGGTGAGCGACTGGTTG;

No. 22 primer set H F:
CAGTACATGGC(C/T)GAAACCTTGAC;
```

-continued

No. 23 primer set I F:
CGAGTTCTCGTTCCGCG;

No. 24 primer set I R:
GTTAGAACGCGTAATACGAC;

No. 25 primer set J F:
ATCGCCAACCACTTCGC;

No. 26 primer set J R:
GTAATACGACTCACTATAGG;
and

No. 27 common sequence of NucS:
ALPTPVSAATAR.

Receipt Number
   *Streptomyces* sp. MBE174 FERM P-21987

---

The invention claimed is:

1. A method of degrading nucleic acids comprising:
providing a sample comprising nucleic acids; and
contacting the sample with a purified nuclease under conditions sufficient to degrade the nucleic acids;
wherein the purified nuclease has the amino acid sequence of SEQ ID NO:1 or SEQ ID NO:2.

2. The method according to claim 1, wherein the nucleic acids are DNA.

3. The method according to claim 1, wherein the purified nuclease is purified from bacteria of the genus *Streptomyces*.

4. The method according to claim 1, wherein substrates of the nuclease comprise double-stranded DNA, single-stranded DNA, and RNA.

5. The method according to claim 1, wherein the nuclease has a specific activity that is at least 90% of the specific activity of BENZONASE (Registered Trademark) when the nuclease is purified, and
wherein the specific activity is measured by determining the specific activity of the purified nuclease and the specific activity of the BENZONASE (Registered Trademark) when subjected to double-stranded DNA for 30 minutes at 37 degrees Celsius in 20 mM of Tris/HCl at pH 8.5 that comprises 1 mM of $MgCl_2$ and 1 mM of $CaCl_2$.

6. The method according to claim 1, wherein the nuclease requires $Mg^{2+}$ or $Mn^{2+}$ as divalent metal ion.

7. The method according to claim 1, wherein substrates of the nuclease comprise double-stranded DNA, single-stranded DNA, and RNA,
wherein the nuclease is purified from bacteria of the genus *Streptomyces*,
wherein the nuclease has a specific activity that is at least 90% of the specific activity of BENZONASE (Registered Trademark) when the nuclease is purified, and
wherein the specific activity is measured by determining the specific activity of the purified nuclease and the specific activity of the BENZONASE (Registered Trademark) when subjected to double-stranded DNA for 30 minutes at 37 degrees Celsius in 20 mM of Tris/HCl at pH 8.5 that comprises 1 mM of $MgCl_2$ and 1 mM of $CaCl_2$, and
wherein the nuclease requires $Mg^{2+}$ or $Mn^{2+}$ as divalent metal ion.

8. The method of claim 1, wherein the purified nuclease of SEQ ID NO: 1 or SEQ ID NO: 2 is expressed from an expression vector comprising the nucleic acids that code for SEQ ID NO: 1 or SEQ ID NO: 2, wherein the nucleic acids that code for SEQ ID NO:1 or SEQ ID NO: 2 are operably linked to an expression control sequence, wherein the expression control sequence comprises a drug resistance gene.

* * * * *

SEQUENCE LISTING

<160> NUMBER OF SEQ ID NOS: 27

<210> SEQ ID NO 1
<211> LENGTH: 157
<212> TYPE: PRT
<213> ORGANISM: Streptmyces sp. MBE174

<400> SEQUENCE: 1

Ala Leu Pro Thr Pro Val Ser Ala Ala Thr Ala Arg Gly Tyr Leu Ala
1               5                   10                  15

Ser Leu Lys Val Ala Pro Glu Asn Arg Thr Gly Tyr Lys Arg Asp Leu
            20                  25                  30

Phe Pro His Trp Ile Thr Gln Ser Gly Thr Cys Asn Thr Arg Glu Thr
        35                  40                  45

Val Leu Lys Arg Asp Gly Thr Asn Val Val Thr Asp Ala Ala Cys Ala
    50                  55                  60

Ala Thr Ser Gly Ser Trp Tyr Ser Pro Phe Asp Gly Ala Thr Trp Thr
65                  70                  75                  80

Ala Ala Ser Asp Val Asp Ile Asp His Leu Val Pro Leu Ala Glu Ala
                85                  90                  95

Trp Asp Ser Gly Ala Ser Ala Trp Thr Thr Ala Gln Arg Gln Ala Phe
            100                 105                 110

Ala Asn Asp Leu Thr Arg Pro Gln Leu Leu Ala Val Thr Asp Thr Val
        115                 120                 125

Asn Gln Ser Lys Gly Asp Lys Asp Pro Ala Glu Trp Met Pro Pro Arg
    130                 135                 140

Ala Ala Tyr His Cys Thr Tyr Val Arg Ala Trp Val Gln
145                 150                 155

<210> SEQ ID NO 2
<211> LENGTH: 575
<212> TYPE: PRT
<213> ORGANISM: Streptmyces sp. MBE174

<400> SEQUENCE: 2

Asp Ser Val Arg Ile His Asp Ile Gln Gly Thr Thr Arg Ile Ser Pro
1               5                   10                  15

Tyr Ala Gly Arg Gln Val Ala Asp Val Pro Gly Val Val Thr Gly Val
            20                  25                  30

Arg Asp His Gly Ser Ser Arg Gly Phe Trp Phe Gln Asp Pro Arg Pro

```
                35                  40                  45
Asp Asp Asp Pro Ala Thr Ser Glu Gly Val Phe Val Phe Thr Gly Ser
 50                      55                  60

Ala Pro Gly Val Glu Ala Gly Asp Ala Val Thr Val Ser Gly Thr Val
 65                  70                  75                  80

Ser Glu Phe Val Pro Gly Gly Thr Ala Ser Gly Asn Gln Ser Leu Thr
                     85                  90                  95

Glu Ile Thr Arg Pro Thr Val Thr Val Val Ser Arg Gly Asn Pro Val
                100                 105                 110

Pro Asp Pro Val Val Val Ser Ala Arg Ser Val Pro His Ala Tyr Ala
            115                 120                 125

Pro Ala Gly Asp Ala Ala Ala Asn Gly Ser Val Asn Ala Leu Pro Leu
            130                 135                 140

Arg Pro Asp Arg Tyr Ala Leu Asp Tyr Tyr Glu Ser Leu Glu Gly Met
145                 150                 155                 160

Asn Val Gln Val Ala Asp Ala Arg Val Val Gly Ala Thr Asp Pro Tyr
                165                 170                 175

Thr Glu Leu Trp Val Thr Val Lys Pro Gly Glu Asn Ala Ser Pro Arg
                180                 185                 190

Gly Gly Thr Val Tyr Gly Ser Arg Asp Ala Gln Asn Thr Gly Arg Leu
            195                 200                 205

Gln Ile Gln Thr Leu Gly Val Pro Ala Gly Phe Pro Ala Ala Asp Val
210                 215                 220

Gly Asp Thr Leu Ala Gly Ala Thr Thr Gly Pro Leu Asp Tyr Asn Gln
225                 230                 235                 240

Phe Gly Gly Tyr Thr Leu Val Ala Arg Ser Leu Gly Thr Leu Thr Ala
                245                 250                 255

Gly Gly Leu Ala Arg Glu Thr Thr Arg Glu Gln His Arg Asp Glu Leu
            260                 265                 270

Ser Val Ala Thr Tyr Asn Val Glu Asn Leu Asp Pro Ser Asp Gly Thr
            275                 280                 285

Phe Ala Ala His Ala Glu Ala Ile Val Arg Asn Leu Arg Ser Pro Asp
290                 295                 300

Ile Val Ser Leu Glu Glu Ile Gln Asp Asp Asn Gly Ala Thr Asp Asp
305                 310                 315                 320

Gly Thr Val Thr Ala Gly Val Thr Val Gly Lys Leu Ile Asp Ala Val
                325                 330                 335

Val Ala Ala Gly Gly Pro Arg Tyr Asp Trp Arg Ser Val Asp Pro Val
            340                 345                 350

Asp Lys Ala Asp Gly Gly Gln Pro Gly Gly Asn Ile Arg Gln Val Phe
            355                 360                 365

Leu Phe Asp Pro Arg Arg Val Ser Phe Ala Asp Arg Pro Gly Gly Asp
            370                 375                 380

Ala Val Thr Ala Thr Gly Val Val Lys Val Arg Gly Lys Ala Ala Leu
385                 390                 395                 400

Thr His Ser Pro Gly Arg Val Asp Pro Ala Asn Pro Ala Trp Leu Asn
                    405                 410                 415

Ser Arg Lys Pro Leu Ala Gly Glu Phe Ser Phe Arg Gly Arg Thr Val
                420                 425                 430

Phe Val Ile Ala Asn His Phe Ala Ser Lys Gly Gly Asp Gln Gly Leu
            435                 440                 445

Thr Ser Gln Tyr Gln Pro Pro Ala Arg Ser Ser Glu Thr Gln Arg His
450                 455                 460
```

```
Leu Gln Ala Thr Ala Val Asn Thr Phe Val Lys Gln Ile Leu Ala Val
465                 470                 475                 480

Gln Lys Asn Ala Asp Val Ile Ala Leu Gly Asp Ile Asn Asp Phe Glu
                485                 490                 495

Phe Ser Gly Thr Thr Glu Arg Leu Glu Ala Gly Gly Ala Leu Trp Ser
                500                 505                 510

Ala Val Arg Ser Leu Pro Pro Gly Glu Arg Tyr Ser Tyr Val Tyr Gln
                515                 520                 525

Gly Asn Ser Gln Val Leu Asp Gln Ile Leu Val Ser Pro Ser Ile Arg
                530                 535                 540

Arg Gly His Leu Ser Tyr Asp Ser Val His Ile Asn Ala Glu Phe His
545                 550                 555                 560

Asp Gln Ile Ser Asp His Asp Pro Gln Val Leu Arg Tyr Arg Pro
                565                 570                 575

<210> SEQ ID NO 3
<211> LENGTH: 214
<212> TYPE: PRT
<213> ORGANISM: Streptmyces sp. MBE174

<400> SEQUENCE: 3

Met Pro Lys Leu Tyr Ala Arg Arg Phe Ala Val Leu Ala Ala Leu
1               5                   10                  15

Thr Gly Leu Ile Ala Ser Ala Gly Leu Phe His Gly Pro Ala Ala Ser
                20                  25                  30

Ala Ala Leu Pro Thr Pro Val Ser Ala Ala Thr Ala Arg Gly Tyr Leu
                35                  40                  45

Ala Ser Leu Lys Val Ala Pro Glu Asn Arg Thr Gly Tyr Lys Arg Asp
50                  55                  60

Leu Phe Pro His Trp Ile Thr Gln Ser Gly Thr Cys Asn Thr Arg Glu
65                  70                  75                  80

Thr Val Leu Lys Arg Asp Gly Thr Asn Val Val Thr Asp Ala Ala Cys
                85                  90                  95

Ala Ala Thr Ser Gly Ser Trp Tyr Ser Pro Phe Asp Gly Ala Thr Trp
                100                 105                 110

Thr Ala Ala Ser Asp Val Asp Ile Asp His Leu Val Pro Leu Ala Glu
                115                 120                 125

Ala Trp Asp Ser Gly Ala Ser Ala Trp Thr Thr Ala Gln Arg Gln Ala
                130                 135                 140

Phe Ala Asn Asp Leu Thr Arg Pro Gln Leu Leu Ala Val Thr Asp Thr
145                 150                 155                 160

Val Asn Gln Ser Lys Gly Asp Lys Asp Pro Ala Glu Trp Met Pro Pro
                165                 170                 175

Arg Ala Ala Tyr His Cys Thr Tyr Val Arg Ala Trp Val Gln Val Lys
                180                 185                 190

Tyr Tyr Tyr Gly Leu Ser Val Asp Thr Ala Glu Lys Thr Ala Leu Thr
                195                 200                 205

Asn Arg Leu Ala Gly Cys
    210

<210> SEQ ID NO 4
<211> LENGTH: 607
<212> TYPE: PRT
<213> ORGANISM: Streptmyces sp. MBE174

<400> SEQUENCE: 4
```

```
Met Ala Ser Gln Ser Val Thr Arg Leu Ala Ala Leu Thr Val Ala Ala
1               5                   10                  15

Thr Cys Ser Ala Ala Ser Val Val Leu Gly Pro Pro Ala His Ala
            20                  25                  30

Asp Ser Val Arg Ile His Asp Ile Gln Gly Thr Thr Arg Ile Ser Pro
            35                  40                  45

Tyr Ala Gly Arg Gln Val Ala Asp Val Pro Gly Val Val Thr Gly Val
50                  55                  60

Arg Asp His Gly Ser Ser Arg Gly Phe Trp Phe Gln Asp Pro Arg Pro
65                  70                  75                  80

Asp Asp Asp Pro Ala Thr Ser Glu Gly Val Phe Val Phe Thr Gly Ser
                85                  90                  95

Ala Pro Gly Val Glu Ala Gly Asp Ala Val Thr Val Ser Gly Thr Val
                100                 105                 110

Ser Glu Phe Val Pro Gly Gly Thr Ala Ser Gly Asn Gln Ser Leu Thr
            115                 120                 125

Glu Ile Thr Arg Pro Thr Val Thr Val Ser Arg Gly Asn Pro Val
130                 135                 140

Pro Asp Pro Val Val Ser Ala Arg Ser Val Pro His Ala Tyr Ala
145                 150                 155                 160

Pro Ala Gly Asp Ala Ala Asn Gly Ser Val Asn Ala Leu Pro Leu
                165                 170                 175

Arg Pro Asp Arg Tyr Ala Leu Asp Tyr Tyr Glu Ser Leu Glu Gly Met
                180                 185                 190

Asn Val Gln Val Ala Asp Ala Arg Val Val Gly Ala Thr Asp Pro Tyr
            195                 200                 205

Thr Glu Leu Trp Val Thr Val Lys Pro Gly Glu Asn Ala Ser Pro Arg
210                 215                 220

Gly Gly Thr Val Tyr Gly Ser Arg Asp Ala Gln Asn Thr Gly Arg Leu
225                 230                 235                 240

Gln Ile Gln Thr Leu Gly Val Pro Ala Gly Phe Pro Ala Ala Asp Val
            245                 250                 255

Gly Asp Thr Leu Ala Gly Ala Thr Thr Gly Pro Leu Asp Tyr Asn Gln
            260                 265                 270

Phe Gly Gly Tyr Thr Leu Val Ala Arg Ser Leu Gly Thr Leu Thr Ala
            275                 280                 285

Gly Gly Leu Ala Arg Glu Thr Thr Arg Glu Gln His Arg Asp Glu Leu
            290                 295                 300

Ser Val Ala Thr Tyr Asn Val Glu Asn Leu Asp Pro Ser Asp Gly Thr
305                 310                 315                 320

Phe Ala Ala His Ala Glu Ala Ile Val Arg Asn Leu Arg Ser Pro Asp
                325                 330                 335

Ile Val Ser Leu Glu Glu Ile Gln Asp Asp Asn Gly Ala Thr Asp Asp
            340                 345                 350

Gly Thr Val Thr Ala Gly Val Thr Val Gly Lys Leu Ile Asp Ala Val
            355                 360                 365

Val Ala Ala Gly Gly Pro Arg Tyr Asp Trp Arg Ser Val Asp Pro Val
370                 375                 380

Asp Lys Ala Asp Gly Gly Gln Pro Gly Gly Asn Ile Arg Gln Val Phe
385                 390                 395                 400

Leu Phe Asp Pro Arg Arg Val Ser Phe Ala Asp Arg Pro Gly Gly Asp
                405                 410                 415
```

Ala Val Thr Ala Thr Gly Val Val Lys Val Arg Gly Lys Ala Ala Leu
            420             425                 430

Thr His Ser Pro Gly Arg Val Asp Pro Ala Asn Pro Ala Trp Leu Asn
            435                 440                 445

Ser Arg Lys Pro Leu Ala Gly Glu Phe Ser Phe Arg Gly Arg Thr Val
        450                 455                 460

Phe Val Ile Ala Asn His Phe Ala Ser Lys Gly Asp Gln Gly Leu
465                 470                 475                 480

Thr Ser Gln Tyr Gln Pro Pro Ala Arg Ser Glu Thr Gln Arg His
                485                 490                 495

Leu Gln Ala Thr Ala Val Asn Thr Phe Val Lys Gln Ile Leu Ala Val
            500                 505                 510

Gln Lys Asn Ala Asp Val Ile Ala Leu Gly Asp Ile Asn Asp Phe Glu
            515                 520                 525

Phe Ser Gly Thr Thr Glu Arg Leu Glu Ala Gly Gly Ala Leu Trp Ser
        530                 535                 540

Ala Val Arg Ser Leu Pro Pro Gly Glu Arg Tyr Ser Tyr Val Tyr Gln
545                 550                 555                 560

Gly Asn Ser Gln Val Leu Asp Gln Ile Leu Val Ser Pro Ser Ile Arg
                565                 570                 575

Arg Gly His Leu Ser Tyr Asp Ser Val His Ile Asn Ala Glu Phe His
            580                 585                 590

Asp Gln Ile Ser Asp His Asp Pro Gln Val Leu Arg Tyr Arg Pro
            595                 600                 605

<210> SEQ ID NO 5
<211> LENGTH: 645
<212> TYPE: DNA
<213> ORGANISM: Streptmyces sp. MBE174

<400> SEQUENCE: 5

```
atgccgaagc tctacgcgcg tcgacggttc gccgtcctcg ccgcgctcac cggactcata    60
gcctccgccg ggctcttcca cggtccggcc gcctccgccg ccctcccac gccggtcagc   120
gccgccaccg cccgcggcta cctcgcctcc ctgaaggtgg ccccccgagaa ccgcaccggc   180
tacaagcgcg acctcttccc ccactggatc acgcagtccg gcacctgcaa cacccgcgag   240
accgtcctca aacgcgacgg caccaacgtc gtcaccgacg ccgcctgcgc cgccaccagc   300
ggcagttggt actcgcccctt cgacggggcc acctggaccg ccgcctccga cgtcgacatc   360
gaccacctcg tcccgctggc cgaggcgtgg gactccggcg cgagcgcctg gaccacggcc   420
cagcgccagg cgttcgccaa cgacctgaca cgtcctcagc tcctcgccgt caccgacacc   480
gtgaaccagt ccaagggcga caaggacccg gccgagtgga tgccgccccg gccgcctac   540
cactgcacct acgtacgcgc ctgggtgcag gtgaagtact actacggcct ctcggtcgac   600
accgccgaga agacggcgct cacgaaccgg ctcgccggct gctga                   645
```

<210> SEQ ID NO 6
<211> LENGTH: 1824
<212> TYPE: DNA
<213> ORGANISM: Streptmyces sp. MBE174

<400> SEQUENCE: 6

```
ttggccagcc agtccgtcac gcgcctcgcc gcgctcaccg tcgccgccac ctgttcggcg    60
gcgtccgtcg tcgtcctcgg tccgcccgcg cacgccgact ccgtgcgcat ccacgacatc   120
cagggcacca ccaggatctc cccgtacgcc ggccgccagg tcgccgacgt gcccggcgtc   180
```

```
gtcaccggag tccgcgacca cggctcctcc cggggcttct ggttccagga cccgcggccc      240
gacgacgacc ccgccaccag cgagggagtg ttcgtcttca ccggctcggc ccccggggtc      300
gaggccggcg acgcggtcac cgtctccggc acggtctcgg agttcgtgcc cggcgggacc      360
gcctccggca accagtcgct caccgagatc acccggccca cggtcaccgt ggtctcccgc      420
ggcaacccgg tgccggaccc ggtcgtcgtc tcggcccgct ccgtgccgca cgcctacgcc      480
ccggcgggcg acgccgccgc gaacggctcc gtcaacgccc tgccctgcg gcccgaccgc       540 tacgccctgg actactacga gtccctggag ggcatgaacg tccaggtggc cgacgcccgc      600
gtggtcggcg cgaccgaccc gtacaccgag ctgtgggtga cggtgaagcc cggcgagaac      660
gcgagccccc ggggcggcac cgtctacggc tcccgcgacg cgcagaacac cgggcggctg      720
cagatccaga ccctgggcgt accagccggc ttccccgccg ccgacgtggg cgacacccte      780 gcgggcgcca ccaccggccc gctcgactac aaccagttcg gcggctacac cctggtcgcc      840
cgtagtctcg gcacgctcac cgccggcggg ctcgcccgcg agacgacccg ggagcagcac      900
cgcgacgagc tgtcggtggc cacgtacaac gtcgagaacc tcgaccccte cgacggcacc      960 ttcgccgcgc acgcggaggc gatcgtccgg aacctgcgct caccggacat cgtgtccctg     1020
gaggagatcc aggacgacaa cggcgccacg gacgacggca cggtgaccgc cggcgtgacg     1080
gtgggcaagc tgatcgacgc cgtcgtgcgg ccggcggcc cgcgctacga ctggcgctcg      1140
gtggaccccg tcgacaaggc ggacggcggg cagccgggcg gcaacatccg ccaggtgttc     1200
ctcttcgacc cgcggcgggt ctccttcgcc gaccgtcccg gcggggacgc ggtcaccgcg     1260
accggggtgg tgaaggtgcg cggcaaggcg gcgctgaccc actccccgg ccgggtcgac      1320 cccgcgaacc ccgcctggct gaacagccgc aagccgctgg ccggcgagtt ctcgttccgc     1380
gggcggacgg tcttcgtgat cgccaaccac ttcgcgtcca agggcggcga ccaggggctg     1440
acctcccagt accagccgcc ggcgcggagt tcggagaccc agcgccacct ccaggcgacg     1500
gcggtgaaca ccttcgtcaa gcagatcctg gcggtccaga gaacgcgga cgtcatcgcc      1560 ctcggcgaca tcaacgactt cgagttctcc ggcacgacgg aacgctgga ggccggcggc      1620 gcgctctggt cggcggtcag gtcgctgccg ccgggcgagc gctactcgta cgtctaccag     1680
ggcaacagcc aggtgctcga ccagatcctg gtgagcccgt cgatccggcg cgggcacctg     1740
tcctacgaca gcgtgcacat caacgccgag ttccacgacc agatcagcga ccacgacccg     1800
caggtgctgc ggtaccgccc ctga                                             1824
```

<210> SEQ ID NO 7
<211> LENGTH: 19
<212> TYPE: DNA
<213> ORGANISM: Artificial sequence
<220> FEATURE:
<223> OTHER INFORMATION: primer

<400> SEQUENCE: 7
cgcatgycda agktctacg                                                    19

<210> SEQ ID NO 8
<211> LENGTH: 15
<212> TYPE: DNA
<213> ORGANISM: Artificial sequence
<220> FEATURE:
<223> OTHER INFORMATION: primer

<400> SEQUENCE: 8
adctgccgct ggtgg                                                      15

<210> SEQ ID NO 9
<211> LENGTH: 17
<212> TYPE: DNA
<213> ORGANISM: Artificial sequence
<220> FEATURE:
<223> OTHER INFORMATION: primer

<400> SEQUENCE: 9
agcggcagyt ggtactc                                                    17

<210> SEQ ID NO 10
<211> LENGTH: 17
<212> TYPE: DNA
<213> ORGANISM: Artificial sequence
<220> FEATURE:
<223> OTHER INFORMATION: primer

<400> SEQUENCE: 10
acccgcgatc tggaagg                                                    17

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
gctacaagcg cgacctcttc                                                 20

<210> SEQ ID NO 12
<211> LENGTH: 19
<212> TYPE: DNA
<213> ORGANISM: Artificial sequence
<220> FEATURE:
<223> OTHER INFORMATION: primer

<400> SEQUENCE: 12
tggactggtt cacggtgtc                                                  19

<210> SEQ ID NO 13
<211> LENGTH: 15
<212> TYPE: DNA
<213> ORGANISM: Artificial sequence
<220> FEATURE:
<223> OTHER INFORMATION: primer

<400> SEQUENCE: 13
aactgccgct ggtgg                                                      15

<210> SEQ ID NO 14
<211> LENGTH: 21
<212> TYPE: DNA
<213> ORGANISM: Artificial sequence
<220> FEATURE:
<223> OTHER INFORMATION: primer

<400> SEQUENCE: 14
ctgagcagta tgtcgacggt c                                               21

<210> SEQ ID NO 15
<211> LENGTH: 20
<212> TYPE: DNA
<213> ORGANISM: Artificial sequence

```
<220> FEATURE:
<223> OTHER INFORMATION: primer

<400> SEQUENCE: 15
gctacaagcg cgacctcttc                                              20

<210> SEQ ID NO 16
<211> LENGTH: 20
<212> TYPE: DNA
<213> ORGANISM: Artificial sequence
<220> FEATURE:
<223> OTHER INFORMATION: primer

<400> SEQUENCE: 16
gttagaacgc gtaatacgac                                              20

<210> SEQ ID NO 17
<211> LENGTH: 22
<212> TYPE: DNA
<213> ORGANISM: Artificial sequence
<220> FEATURE:
<223> OTHER INFORMATION: primer

<400> SEQUENCE: 17
ctgggtgcag gtgaagtact ac                                           22

<210> SEQ ID NO 18
<211> LENGTH: 20
<212> TYPE: DNA
<213> ORGANISM: Artificial sequence
<220> FEATURE:
<223> OTHER INFORMATION: primer

<400> SEQUENCE: 18
gtaatacgac tcactatagg                                              20

<210> SEQ ID NO 19
<211> LENGTH: 20
<212> TYPE: DNA
<213> ORGANISM: Artificial sequence
<220> FEATURE:
<223> OTHER INFORMATION: primer

<400> SEQUENCE: 19
ggcttctgga tvcaggaccc                                              20

<210> SEQ ID NO 20
<211> LENGTH: 16
<212> TYPE: DNA
<213> ORGANISM: Artificial sequence
<220> FEATURE:
<223> OTHER INFORMATION: primer

<400> SEQUENCE: 20
ctgcgggtcg tggtcg                                                  16

<210> SEQ ID NO 21
<211> LENGTH: 17
<212> TYPE: DNA
<213> ORGANISM: Artificial sequence
<220> FEATURE:
<223> OTHER INFORMATION: primer

<400> SEQUENCE: 21
cggtgagcga ctggttg                                                 17
```

```
<210> SEQ ID NO 22
<211> LENGTH: 23
<212> TYPE: DNA
<213> ORGANISM: Artificial sequence
<220> FEATURE:
<223> OTHER INFORMATION: primer

<400> SEQUENCE: 22
cagtacatgg cygaaacctt gac                                              23

<210> SEQ ID NO 23
<211> LENGTH: 17
<212> TYPE: DNA
<213> ORGANISM: Artificial sequence
<220> FEATURE:
<223> OTHER INFORMATION: primer

<400> SEQUENCE: 23
cgagttctcg ttccgcg                                                     17

<210> SEQ ID NO 24
<211> LENGTH: 20
<212> TYPE: DNA
<213> ORGANISM: Artificial sequence
<220> FEATURE:
<223> OTHER INFORMATION: primer

<400> SEQUENCE: 24
gttagaacgc gtaatacgac                                                  20

<210> SEQ ID NO 25
<211> LENGTH: 17
<212> TYPE: DNA
<213> ORGANISM: Artificial sequence
<220> FEATURE:
<223> OTHER INFORMATION: primer

<400> SEQUENCE: 25
atcgccaacc acttcgc                                                     17

<210> SEQ ID NO 26
<211> LENGTH: 20
<212> TYPE: DNA
<213> ORGANISM: Artificial sequence
<220> FEATURE:
<223> OTHER INFORMATION: primer

<400> SEQUENCE: 26
gtaatacgac tcactatagg                                                  20

<210> SEQ ID NO 27
<211> LENGTH: 12
<212> TYPE: PRT
<213> ORGANISM: Streptmyces sp. MBE174

<400> SEQUENCE: 27

Ala Leu Pro Thr Pro Val Ser Ala Ala Thr Ala Arg
1               5                   10
```